United States Patent
Okumura et al.

(10) Patent No.: US 6,372,749 B1
(45) Date of Patent: Apr. 16, 2002

(54) PYRAZOLO[1,5-A]PYRIMIDINE DERIVATIVES

(75) Inventors: Takashi Okumura; Yasuo Shoji; Tadao Shibutani; Tsuneo Yasuda, all of Naruto; Takeshi Iwamoto, Komatsushima, all of (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 0 days.

(21) Appl. No.: 09/700,764

(22) PCT Filed: May 17, 1999

(86) PCT No.: PCT/JP99/02572

§ 371 Date: Nov. 20, 2000

§ 102(e) Date: Nov. 20, 2000

(87) PCT Pub. No.: WO99/59998

PCT Pub. Date: Nov. 25, 1999

(30) Foreign Application Priority Data

May 19, 1998 (JP) .......................... 10-136960

(51) Int. Cl.$^7$ .......................... C07D 487/04
(52) U.S. Cl. .................... 514/258; 544/281
(58) Field of Search ................ 514/258; 544/281

(56) References Cited

FOREIGN PATENT DOCUMENTS

| JP | 3-204877 | 9/1991 |
|----|----------|--------|
| JP | 7-309872 | 11/1995 |
| JP | 8-3167 | 1/1996 |
| JP | 8-310951 | 11/1996 |
| JP | 8-311068 | 11/1996 |
| JP | 10-101671 | 4/1998 |
| JP | 10-114774 | 5/1998 |
| WO | 96/32394 | 10/1996 |
| WO | 97/11946 | 4/1997 |

OTHER PUBLICATIONS

Abraham Thomas, Manjaree Chakraborty, Hiriyakkanavar Ila, Hiriyakkanavar Junjappa, "Cyclocondensation of Oxoketene Dithioacetals with 3–Aminopyrazoles: A Facile Highly Regioselective General Route to Substituted and Fused Pyrazolo[a]Pyrimidines", Tetrahedron, 1990, vol. 46, No. 2, pp. 577–586.

*Primary Examiner*—John M. Ford
(74) *Attorney, Agent, or Firm*—Sughrue Mion, PLLC

(57) ABSTRACT

The present invention provides pyrazolo[1,5-a]pyrimidine derivatives represented by the formula (1)

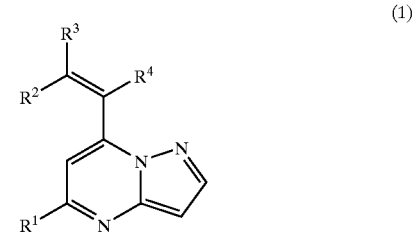

(1)

wherein $R^1$ represents lower alkyl or the like; one of $R^2$ and $R^3$ represents hydrogen and the other represents phenyl having lower alkoxy or the like, and $R^4$ is hydrogen, carboxyl, lower alkoxy-carbonyl or the like. The derivatives of the invention have pharmacological effects such as analgesic action, inhibitory effect on nitrogen monoxide synthetase and the like and are useful as analgesics. The derivatives of the invention are also useful as therapeutic or prophylactic agents for septicemia, endotoxin shock, chronic articular rheumatism, etc.

11 Claims, No Drawings

PYRAZOLO[1,5-A]PYRIMIDINE DERIVATIVES

CROSS REFERENCE TO RELATED APPLICATIONS

Applicants claim priority under 35 U.S.C. §119 of RUSSIA Application No. 98109664 filed on May 19, 1998. Applicants also claim priority under 35 U.S.C. §120 of PCT/RU99/00166 filed on May 19, 1999. The international application under PCT article 21(2) was not published in English.

TECHNICAL FIELD

The present invention relates to novel pyrazolo[1,5-a] pyrimidine derivatives.

BACKGROUND ART

The pyrazolo[1,5-a]pyrimidine derivatives of the invention are novel compounds that have never been described in the literature.

DISCLOSURE OF INVENTION

An object of the present invention is to provide compounds useful as medicine.

The present invention provides novel pyrazolo[1,5-a] pyrimidine derivatives represented by the following formula (1)

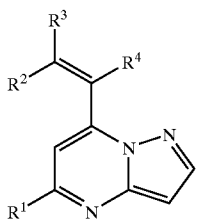

(1)

wherein $R^1$ is lower alkyl, phenyl or thienyl;

one of $R^2$ and $R^3$ is hydrogen and the other is naphthyl, furyl, pyridyl, styryl, phenylethynyl, substituted phenyl having 1 to 3 substituents selected from the group consisting of lower alkoxy, phenyl-lower alkoxy and hydroxyl, or phenyl which may have a substituent selected from the group consisting of lower alkylthio, N,N-di-lower alkylamino, halogen-substituted lower alkyl, phenyl, nitro, methylenedioxy and halogen;

$R^4$ is hydrogen, lower alkylthio, lower alkylsulfinyl, lower alkylsulfonyl, carboxyl, lower alkoxy-carbonyl, lower alkyl, phenylthiomethoxycarbonyl, substituted benzyloxycarbonyl having 1 to 3 substituents selected from the group consisting of lower alkoxy, halogen and nitro, phenoxycarbonyl which may have halogen or nitro as a substituent, carbamoyl, N-lower alkylcarbamoyl, N-benzylcarbamoyl, N-(lower alkoxycarbonyl-lower alkyl)carbamoyl, N-(carboxy-lower alkyl)carbamoyl, N-halophenylcarbamoyl, N-(1-lower alkoxy-carbonyl-2-phenylethyl)carbamoyl, N-(1-carboxy-2-phenylethyl)carbamoyl, phenyl which may have halogen as a substituent, or the group

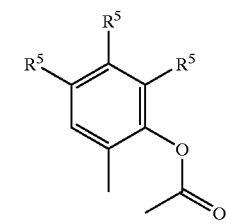

wherein $R^1$, $R^2$ and $R^3$ are as defined above.

When $R^2$ is hydrogen, $R^3$ and $R^4$ may conjointly form a group represented by wherein the $R^5$s are the same or different and independently represent hydrogen or lower alkoxy.

In the specification, the term "lower alkyl" includes alkyl groups having 1 to 6 carbon atoms, such as methyl, ethyl, propyl, butyl, isobutyl, tert-butyl, pentyl, hexyl and the like.

The thienyl group include 2-thienyl and 3-thienyl.

The naphthyl group includes 1-naphthyl and 2-naphthyl.

The furyl group includes 2-furyl and 3-furyl.

The pyridyl group includes 2-pyridyl, 3-pyridyl and 4-pyridyl.

The lower alkoxy group includes alkoxy groups having 1 to 6 carbon atoms, for example, methoxy, ethoxy, propoxy, isopropoxy, butoxy, pentyloxy, hexyloxy and the like.

The phenyl-lower alkoxy group as a substituent of the substituted phenyl group includes phenyl-substituted alkoxy groups having 1 to 6 carbon atoms, for example, benzyloxy, 1-phenylethoxy, 2-phenylethoxy, 3-phenylpropoxy, 4-phenylbutoxy, 5-phenylpentyloxy, 6-phenylhexyloxy and the like.

The substituted phenyl group having 1 to 3 substituents selected from the group consisting of lower alkoxy, phenyl-lower alkoxy and hydroxyl include 2-methoxyphenyl, 3-methoxyphenyl, 4-methoxyphenyl, 4-ethoxyphenyl, 4-propoxyphenyl, 4-buthoxyphenyl, 4-pentyloxyphenyl, 4-hexyloxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 3,4-diethoxyphenyl, 3,4-dipropoxyphenyl, 3,4-dibutoxyphenyl, 3,4-dipentyloxyphenyl, 3,4-dihexyloxyphenyl, 3,4,5-trimethoxyphenyl, 2,3,4-trimethoxyphenyl, 2,3,5-trimethoxyphenyl, 2,3,6-trimethoxyphenyl, 2,4,6-trimethoxyphenyl, 2,4,5-trimethoxyphenyl, 3,4,5-triethoxyphenyl, 3,4,5-tripropoxyphenyl, 3,4,5-tributoxyphenyl, 3,4,5-tripentyloxyphenyl, 3,4,5-trihexyloxyphenyl, 2-hydroxyphenyl, 3-hydroxyphenyl, 4-hydroxyphenyl, 2-benzyloxyphenyl, 3-benzyloxyphenyl, 4-benzyloxyphenyl, 4-(2-phenylethoxy)phenyl, 4-(3-phenylpropoxy)phenyl, 4-(4-phenylbutoxy)phenyl, 4-(5-phenylpentyloxy)phenyl, 4-(6-phenylhexyloxy)phenyl, 4-hydroxy-3-methoxyphenyl, 3-hydroxy-4-methoxyphenyl, 4-benzyloxy-3-methoxyphenyl, 3-benzyloxy-4-methoxyphenyl, 4-benzyloxy-3-hydroxyphenyl, 3-benzyloxy-4-hydroxyphenyl, 3-hydroxy-4,5-dimethoxyphenyl, 4-hydroxy-3,5-dimethoxyphenyl, 3-benzyloxy-4,5-dimethoxyphenyl, 4-benzyloxy-3,5-dimethoxyphenyl, 3,4-dihydroxyphenyl, 3,4-dibenzyloxyphenyl, 3,4,5-trihydroxyphenyl, 3,4,5-tribenzyloxyphenyl and the like.

The lower alkylthio group as a substituent on the phenyl group which may have a substituent selected from the group consisting of lower alkylthio, N,N-di-lower alkylamino, halogen-substituted lower alkyl, phenyl, nitro, methylenedioxy and halogen includes, for example, alkylthio groups having 1 to 6 carbon atoms, such as methylthio, ethylthio, propylthio, butylthio, pentylthio, hexylthio and the like.

The N,N-di-lower alkylamino group as a substituent on the phenyl group includes, for example, N,N-di-($C_{1-6}$-alkyl) amino groups such as N,N-dimethylamino, N,N-diethylamino, N,N-dipropylamino, N,N-dibutylamino, N,N-dipentylamino, N,N-dihexylamino and the like.

The halogen-substituted lower alkyl group as a substituent on the phenyl group includes, for example, perhalogeno-($C_{1-6}$-alkyl) groups (wherein halogeno is selected from fluorine, chlorine, bromine and iodine). Specific examples include trifluoromethyl, pentafluoroethyl, heptafluoropropyl, nonafluorobutyl, undecafluoropentyl, tridecafluorohexyl and the like.

The halogen atom as a substituent on the phenyl group includes fluorine, chlorine, bromine and iodine.

Examples of the phenyl group which may have a substituent selected from the group consisting of lower alkylthio, N,N-di-lower alkylamino, halogen-substituted lower alkyl, phenyl, nitro, methylenedioxy and halogen are unsubstituted phenyl, 2-methylthiophenyl, 3-methylthiophenyl, 4-methylthiophenyl, 4-ethylthiophenyl, 4-propylthiophenyl, 4-butylthiophenyl, 4-pentylthiophenyl, 4-hexylthiophenyl, 2-(N,N-dimethylamino)phenyl, 3-(N,N-dimethylamino)phenyl, 4-(N,N-dimethylamino)phenyl, 4-(N,N-diethylamino) phenyl, 4-(N,N-dipropylamino)phenyl, 4-(N,N-dibutylamino)phenyl, 4-(N,N-dipentylamino)phenyl, 4-(N,N-dihexylamino)phenyl, 2-trifluoromethylphenyl, 3-trifluoromethylphenyl, 4-trifluoromethylphenyl, 4-pentafluoroethylphenyl, 4-heptafluoropropylphenyl, 4-nonafluorobutylphenyl, 4-undecafluoropentylphenyl, 4-tridecafluorohexylphenyl, 2-biphenylyl, 3-biphenylyl, 4-biphenylyl, 2-nitrophenyl, 3-nitrophenyl, 4-nitrophenyl, 2,3-methylenedioxyphenyl, 3,4-methylenedioxyphenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-fluorophenyl, 3-fluorophenyl, 4-fluorophenyl and the like.

Examples of the lower alkylthio group include those mentioned above as a substituent on the phenyl group.

The lower alkylsulfinyl group includes, for example, ($C_{1-6}$-alkyl)sulfinyl groups such as methylsulfinyl, ethylsulfinyl, propylsulfinyl, butylsulfinyl, pentylsulfinyl, hexylsulfinyl and the like.

The lower alkylsulfonyl group includes, for example, ($C_{1-6}$-alkyl)sulfonyl groups such as methylsulfonyl, ethylsulfonyl, propylsulfonyl, butylsulfonyl, pentylsulfonyl, hexylsulfonyl and the like.

The lower alkoxy-carbonyl group includes ($C_{1-6}$-alkoxy) carbonyl groups such as methoxycarbonyl, ethoxycarbonyl, propoxycarbonyl, butoxycarbonyl, pentyloxycarbonyl, hexyloxycarbonyl and the like.

The substituted benzyloxycarbonyl group having 1 to 3 substituents selected from the group consisting of lower alkoxy, halogen and nitro includes, for example, 2-methoxybenzyloxycarbonyl, 3-methoxybenzyloxycarbonyl, 4-methoxybenzyloxycarbonyl, 3-ethoxybenzyloxycarbonyl, 3-propoxybenzyloxycarbonyl, 3-butoxybenzyloxycarbonyl, 3-pentyloxybenzyloxycarbonyl, 3-hexyloxybenzyloxycarbonyl, 2-chlorobenzyloxycarbonyl, 3-chlorobenzyloxycarbonyl, 4-chlorobenzyloxycarbonyl, 4-bromobenzyloxycarbonyl, 4-iodobenzyloxycarbonyl, 4-fluorobenzyloxycarbonyl, 2-nitrobenzyloxycarbonyl, 3-nitrobenzyloxycarbonyl, 4-nitrobenzyloxycarbonyl, 2,3-dimethoxybenzyloxycarbonyl, 2,4-dimethoxybenzyloxycarbonyl, 3,4-dimethoxybenzyloxycarbonyl, 3,5-dimethoxybenzyloxycarbonyl, 2,3-dichlorobenzyloxycarbonyl, 2,4-dichlorobenzyloxycarbonyl, 3,4-dichlorobenzyloxycarbonyl, 3,5-dichlorobenzyloxycarbonyl, 2,4-dinitrobenzyloxycarbonyl, 3,5-dinitrobenzyloxycarbonyl, 2,3,4-trimethoxybenzyloxycarbonyl, 2,3,5-trimethoxybenzyloxycarbonyl, 2,3,6-trimethoxybenzyloxycarbonyl, 2,4,5-trimethoxybenzyloxycarbonyl, 2,4,6-trimethoxybenzyloxycarbonyl, 3,4,5-trimethoxybenzyloxycarbonyl, 2,4,6-trimethoxybenzyloxycarbonyl, 2,4,6-trichlorobenzyloxycarbonyl, 2,4,6-trinitrobenzyloxycarbonyl and the like.

The phenoxycarbonyl group which may have halogen or nitro as a substituent includes, for example, 2-chlorophenoxycarbonyl, 3-chlorophenoxycarbonyl, 4-chlorophenoxycarbonyl, 4-bromophenoxycarbonyl, 4-iodophenoxycarbonyl, 4-fluorophenoxycarbonyl, 2-nitrophenoxycarbonyl, 3-nitrophenoxycarbonyl, 4-nitrophenoxycarbonyl and the like.

The N-lower alkyl-carbamoyl group includes N-($C_{1-6}$-alkyl)carbamoyl groups such as N-methylcarbamoyl, N-ethylcarbamoyl, N-propylcarbamoyl, N-isopropylcarbamoyl, N-butylcarbamoyl, N-pentylcarbamoyl, N-hexylcarbamoyl and the like.

The N-(lower alkoxy-carbonyl-lower alkyl)carbamoyl group includes N-[($C_{1-6}$-alkoxy)carbonyl($C_{1-6}$-alkyl)] carbamoyl groups such as N-(methoxycarbonylmethyl) carbamoyl, N-(ethoxycarbonylmethyl)carbamoyl, N-(propoxycarbonylmethyl)carbamoyl, N-(butoxycarbonylmethyl)carbamoyl, N-(pentyloxycarbonylmethyl)carbamoyl, N-(hexyloxycarbonylmethyl)carbamoyl, N-(2-methoxycarbonylethyl)carbamoyl, N-(3-methoxycarbonylpropyl)carbamoyl, N-(4-methoxycarbonylbutyl)carbamoyl, N-(5-methoxycarbonylpentyl)carbamoyl, N-(6-methoxycarbonylhexyl)carbamoyl and the like.

The N-(carboxy-lower alkyl)carbamoyl group includes N-(carboxy-$C_{1-6}$-alkyl)carbamoyl groups such as N-(carboxymethyl)carbamoyl, N-(2-carboxyethyl) carbamoyl, N-(3-carboxypropyl)carbamoyl, N-(4-carboxybutyl)carbamoyl, N-(5-carboxypentyl)carbamoyl, N-(6-carboxyhexyl)carbamoyl and the like.

The N-halophenylcarbamoyl group includes N-phenylcarbamoyl groups having on the phenyl ring a halogen atom selected from fluorine, chlorine, bromine and iodine.

Specific examples are N-(2-chlorophenyl)carbamoyl, N-(3-chlorophenyl)carbamoyl, N-(4-chlorophenyl) carbamoyl, N-(2-bromophenyl)carbamoyl, N-(3-bromophenyl)carbamoyl, N-(4-bromophenyl)carbamoyl, N-(2-iodophenyl)carbamoyl, N-(3-iodophenyl)carbamoyl, N-(4-iodophenyl)carbamoyl, N-(2-fluorophenyl)carbamoyl, N-(3-fluorophenyl)carbamoyl, N-(4-fluorophenyl)carbamoyl and the like.

The N-(1-lower alkoxy-carbonyl-2-phenylethyl) carbamoyl group includes N-[1-($C_{1-6}$-alkoxy)carbonyl-2-phenylethyl]carbamoyl groups such as N-(1-methoxycarbonyl-2-phenylethyl)carbamoyl, N-(1-ethoxycarbonyl-2-phenylethyl)carbamoyl, N-(1-propoxycarbonyl-2-phenylethyl)carbamoyl, N-(1-butoxycarbonyl-2-phenylethyl)carbamoyl, N-(1-pentyloxycarbonyl-2-phenylethyl)carbamoyl, N-(1-hexyloxycarbonyl-2-phenylethyl)carbamoyl and the like.

The phenyl group which may have halogen as a substituent Includes unsubstituted phenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-fluorophenyl, 3-fluorophenyl, 4-fluorophenyl and the like.

The pyrazolo[1,5-a]pyrimidine derivatives of the present invention have pharmacological effects such as analgesic action, inhibitory effect on nitrogen monoxide synthetase and the like and are useful as analgesics. The derivatives of the invention are also useful as therapeutic or prophylactic agents for septicemia, endotoxin shock, chronic articular rheumatism, etc.

Examples of the derivatives of the invention preferable for medical use include the following (i) and (ii):

(i) compounds of formula (1) wherein $R^1$ is lower alkyl; and (ii) compounds of formula (1) wherein $R^1$ is phenyl or thienyl, one of $R^2$ and $R^3$ is hydrogen and the other is substituted phenyl having 1 to 3 lower alkoxy groups as substituents and $R^4$ is hydrogen, carboxyl or lower alkoxy-carbonyl.

Among the compounds (i), the following compounds (1a), (1b) and (1c) are more preferred:

(1a) compounds wherein $R^1$ is lower alkyl and $R^4$ is hydrogen, carboxyl or lower alkoxy-carbonyl;

(1b) compounds wherein $R^1$ is lower alkyl and one of $R^2$ and $R^3$ is hydrogen and the other is phenyl having 1 to 3 lower alkoxy groups as substituents, $R^4$ is lower alkylthio, lower alkylsulfinyl, lower alkylsulfonyl, lower alkyl, phenylthiomethoxycarbonyl, substituted benzyloxycarbonyl having 1 to 3 substituents selected from the group consisting of lower alkoxy, halogen and nitro, phenoxycarbonyl which may have halogen or nitro as a substituent, carbamoyl, N-lower alkyl-carbamoyl, N-benzylcarbamoyl, N-(lower alkoxy-carbonyl-lower alkyl)carbamoyl, N-(carboxy-lower alkyl)carbamoyl, N-halophenylcarbamoyl, N-(1-lower alkoxy-carbonyl-2-phenylethyl)carbamoyl, or the group

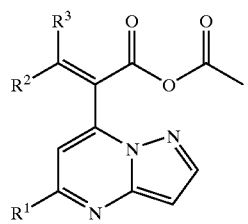

wherein $R^1$, $R^2$ and $R^3$ are as defined in formula (1) and preferably the same as described in this section (1b); and (1c) compounds wherein $R^1$ is lower alkyl and $R^2$ is hydrogen and $R^3$ and $R^4$ conjointly constitute a group represented by

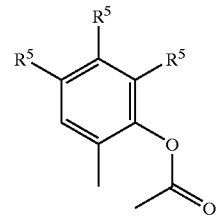

wherein the $R^5$s are the same or different and independently represent hydrogen or lower alkoxy.

Of the compounds (1a) to (1c), especially suitable for medical use are those wherein $R^1$ is lower alkyl, more preferably n-butyl.

More preferred of the compounds (ii) are those wherein $R^1$ is phenyl or thienyl, one of $R^2$ and $R^3$ is hydrogen and the other is phenyl having 1 to 3 lower alkoxy groups as substituents and $R^4$ is hydrogen, carboxyl or lower alkoxy-carbonyl.

Other preferable groups of compounds of the invention include a group of compounds (a) wherein $R^1$ is n-butyl, $R^2$ is hydrogen, $R^3$ is naphthyl, pyridyl, phenyl having 1 to 3 lower alkoxy groups as substituents or halogen-substituted phenyl and $R^4$ is hydrogen or lower alkylthio; and a group of compounds (b) wherein $R^1$ is n-propyl or n-butyl, $R^2$ is substituted phenyl having 1 to 3 substituents selected from the group consisting of lower alkoxy, phenyl-lower alkoxy and hydroxyl, or phenyl which may have a substituent selected from the group consisting of N,N-di-lower alkylamino, halogen-substituted lower alkyl and halogen, $R^3$ is hydrogen and $R^4$ is carboxyl, lower alkoxy-carbonyl, phenylthiomethoxycarbonyl, substituted benzyloxycarbonyl having 1 to 3 substituents selected from the group consisting of lower alkoxy, halogen and nitro, phenoxycarbonyl which may have halogen or nitro as a substituent, or the group

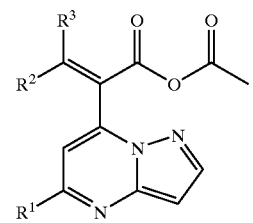

wherein $R^1$, $R^2$ and $R^3$ are as defined above in formula (1) and preferably the same as shown in this section (b).

Most preferable compounds of the invention for medical use include compounds wherein $R^1$ is n-butyl, $R^2$ is hydrogen, $R^3$ is pyridyl, more preferably 2-pyridyl and $R^4$ is hydrogen, and compounds wherein $R^1$ is n-butyl, $R^2$ is phenyl having 3 lower alkoxy groups as substituents or phenyl having 2 lower alkoxy groups and 1 hydroxyl group as substituents, more preferably 3,4,5-trimethoxyphenyl, $R^3$ is hydrogen and $R^4$ is carboxyl.

Methods for producing the derivatives of the invention are described below in detail.

The derivatives of the present invention can be produced, for example, by processes shown below in Reaction Scheme-1 to Reaction Scheme-10.

[Reaction Scheme-1]

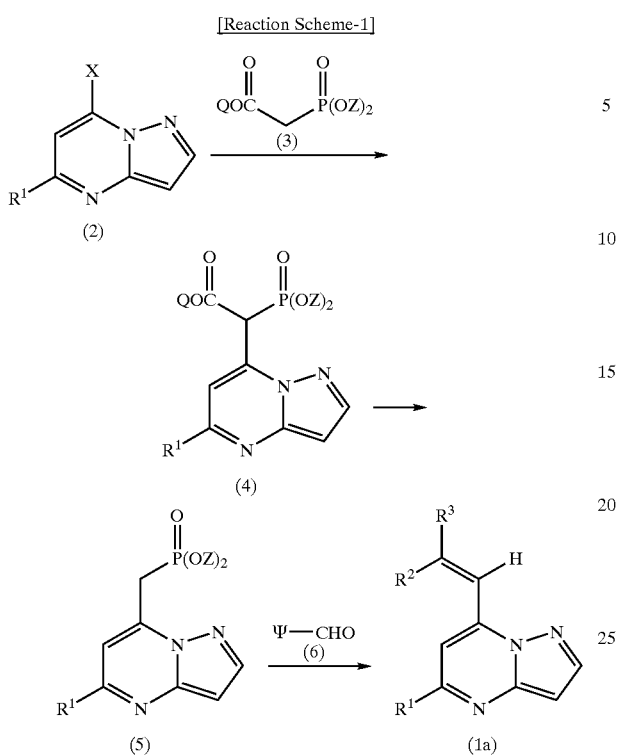

[Reaction Scheme-2]

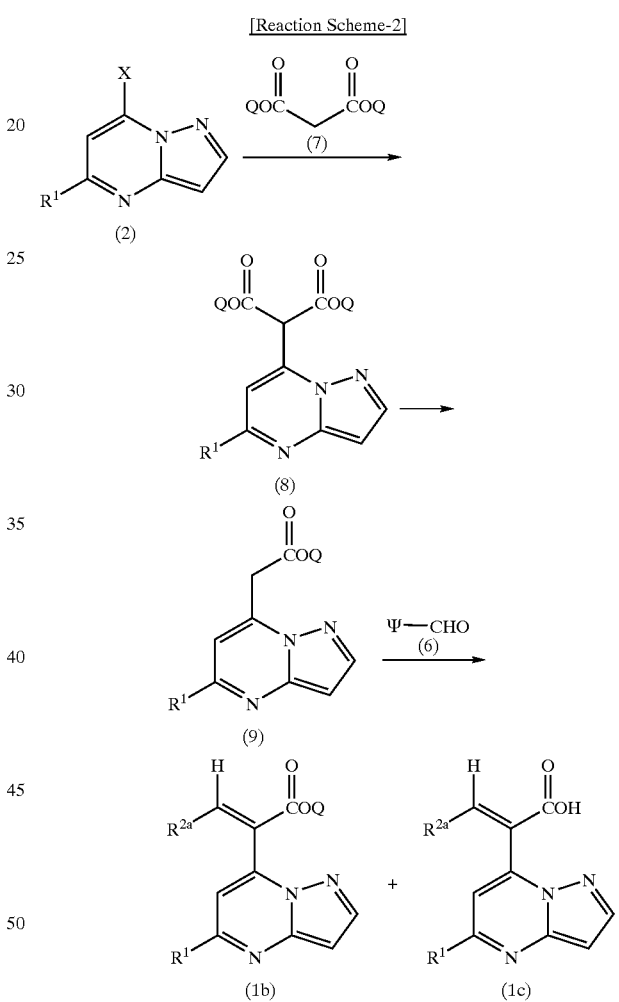

wherein $R^1$, $R^2$ and $R^3$ are as defined above, X represents halogen, Q and Z independently represent lower alkyl, ψ is naphthyl, furyl, pyridyl, styryl, phenylethynyl, substituted phenyl having 1 to 3 substituents selected from the group consisting of lower alkoxy, phenyl-lower alkoxy and hydroxyl, or phenyl which may have a substituent selected from the group consisting of lower alkylthio, N,N-di-lower alkylamino, halogen-substituted lower alkyl, phenyl, nitro, methylenedioxy and halogen.

The halogen atom represented by X includes fluorine, chlorine, bromine and iodine.

According to Reaction Scheme-1, a known compound (2) is reacted with a known compound (3) to produce a compound (4). The compound (4) is converted to a compound (5), which is then reacted with a known compound (6) to produce a compound (1a) of the present invention.

The reaction between the compound (2) and compound (3) can be carried out in the presence of a base in a suitable inert solvent at temperatures in the range of 0° C. to room temperature. Examples of inert solvents include N,N-dimethylformamide (DMF), N,N-dimethylacetamide (DMA), tetrahydrofuran (THF), dimethoxyethane (DME), benzene, toluene and the like. Examples of bases include sodium hydride, potassium hydride, sodium ethoxide, potassium-t-butoxide and the like. Each of the compound (3) and the base is usually used in an equimolar amount to an about 5-fold molar amount, relative to the compound (2). The reaction is completed in about 2 to about 100 hours.

The compound (4) thus obtained is treated with an aqueous alkali solution such as an aqueous sodium hydroxide solution, aqueous potassium hydroxide solution or the like at temperatures in the range of room temperature to about 100° C. for about 30 minutes to about 5 hours, thus converting to the compound (5). Since the aqueous alkali solution functions as a solvent in the above treatment reaction, it is unnecessary to use other solvents. However, other inert solvents such as methanol, ethanol and the like may be used.

The compound (5) resulting from the above reaction is reacted with an aldehyde derivative (6) to convert to a compound (1a) of the present invention. The reaction can be carried out using an aqueous alkali solution such as aqueous sodium hydroxide solution, aqueous potassium hydroxide solution or the like in an inert solvent such as methanol, ethanol or the like at temperatures in the range of about –10° C. to room temperature for about 10 minutes to about 3 hours. Each of the aldehyde derivative (6) and the aqueous alkali solution is used in an equivalent amount to a slight excess, relative to the compound (5).

The reactions for converting the compound (4) to the compound (5) and synthesizing the compound (1a) therefrom shown in Reaction Scheme-1 may be sequentially carried out in the same reactor.

wherein $R^1$, Q, X and ψ are as defined above, $R^{2a}$ is naphthyl, furyl, pyridyl, styryl, phenylethynyl, substituted phenyl having 1 to 3 substituents selected from the group consisting of lower alkoxy, phenyl-lower alkoxy and hydroxyl, or phenyl which may have a substituent selected from the group consisting of lower alkylthio, N,N-di-lower alkylamino, halogen-substituted lower alkyl, phenyl, nitro, methylenedioxy and halogen.

In Reaction Scheme-2, the compound (2) is reacted with a known compound (7) in an inert solvent such as DMF, DMA, THF, DME, benzene, toluene or the like in the presence of a base such as sodium hydride, potassium hydride, sodium ethoxide or the like at 0° C. to about reflux temperature of the solvent. Each of the compound (7) and the base is usually used in an equimolar amount to an about 5-fold molar amount, relative to the compound (2). The reaction is completed in about 1 to about 50 hours.

Subsequently, the diester derivative (8) thus obtained is heated in an inert solvent such as water, water-DMF or the like at about reflux temperature of the solvent for about 3 to about 50 hours, thus converting to a monoester derivative (9).

The reactions for converting the compound (2) to the compound (8) and synthesizing the compound (9) therefrom shown in Reaction Scheme-2 may be sequentially carried out in the same reactor.

The compound (9) resulting from the above reaction is reacted with a known aldehyde derivative (6) using an alkali such as lithium diisopropylamide, lithium dibutyl amide or the like in an inert solvent such as THF, 1,4-dioxane or the like at temperatures in the range of about −100° C. to room temperature for about 5 to about 100 hours. Each of the aldehyde derivative (6) and the alkali is used in an equivalent amount to a slight excess, relative to the compound (5).

[Reaction Scheme-3]

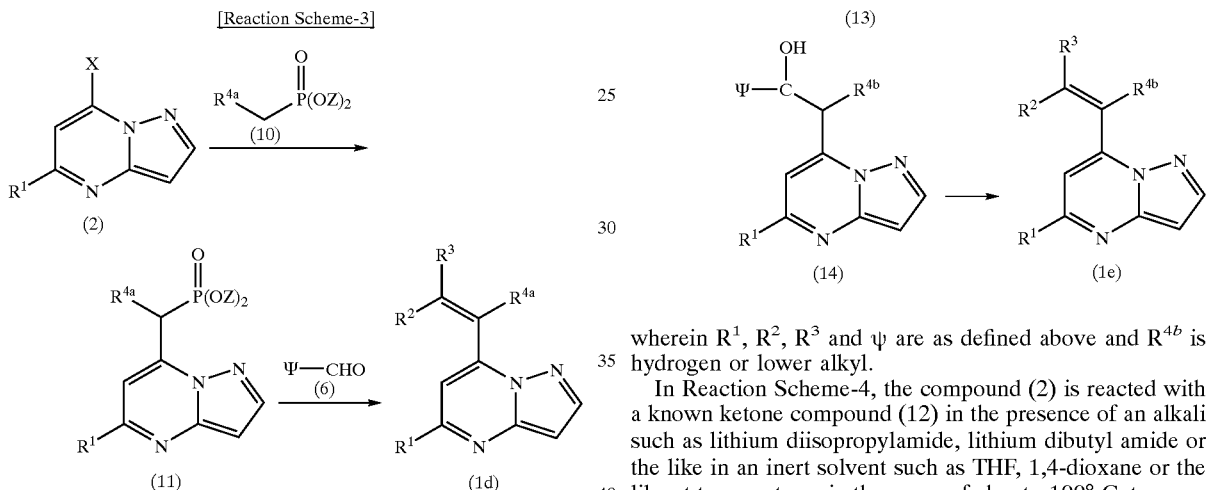

wherein $R^1$, $R^2$, $R^3$, X, Z and ψ are as defined above, $R^{4a}$ is hydrogen, lower alkylthio, lower alkylsulfinyl, lower alkylsulfonyl, lower alkoxy-carbonyl, lower alkyl, phenylthiomethoxycarbonyl, substituted benzyloxycarbonyl having 1 to 3 substituents selected from the group consisting of lower alkoxy, halogen and nitro, phenoxycarbonyl which may have halogen or nitro as a substituent, or phenyl which may have halogen as a substituent.

In Reaction Scheme-3, the compound (2) is reacted with a known compound (10) in an inert solvent such as THF, 1,4-dioxane, diethyl ether, DMF or the like in the presence of a base such as n-butyl lithium, n-hexyl lithium, sodium hydride or the like at temperatures in the range of about −100° C. to room temperature. Each of the compound (10) and the base is usually used in about a slight excess molar to an about 5-fold molar amount, relative to the compound (2). The reaction is completed in about 10 minutes to about 3 hours.

Subsequently, the compound (11) thus obtained is reacted with a known aldehyde derivative (6) to convert to a compound (1d) of the present invention. This reaction can be carried out using an alkali such as sodium hydride, potassium hydride, sodium ethoxide or potassium-t-butoxide in an inert solvent such as dimethoxyethane, diethylene glycol dimethyl ether, t-butanol, THF or the like at room temperature to about reflux temperature of the solvent for about 1 to about 150 hours. Each of the aldehyde derivative (6) and the alkali is used in an equivalent amount to a slight excess, relative to the compound (11).

[Reaction Scheme-4]

wherein $R^1$, $R^2$, $R^3$ and ψ are as defined above and $R^{4b}$ is hydrogen or lower alkyl.

In Reaction Scheme-4, the compound (2) is reacted with a known ketone compound (12) in the presence of an alkali such as lithium diisopropylamide, lithium dibutyl amide or the like in an inert solvent such as THF, 1,4-dioxane or the like at temperatures in the range of about −100° C. to room temperature for about 5 to about 100 hours. Each of the ketone derivative (12) and the alkali is used in a slight molar excess to an about 5-fold molar amount, relative to the compound (2). If necessary, hexamethylphosphoric triamide may be added to the reaction system in a slight molar excess to an about 5-fold molar amount, relative to the compound (2).

Subsequently, the compound (13) thus obtained is subjected to a reduction reaction in a lower alcohol inert solvent such as methanol, ethanol or the like using a boron hydride compound such as sodium borohydride, or in an inert solvent such as diethyl ether, THF or the like using an aluminum hydride compound such as lithium aluminum hydride. Each of the boron hydride compound and the aluminum hydride compound is used in an amount of about 1 to about 6 equivalents, calculated as hydrides. The reaction is completed at temperatures in the range of about 0° C. to room temperature in about 10 minutes to about 3 hours.

Subsequently, the alcohol derivative (14) thus obtained is converted to a compound (1e) of the present invention, for example, by either of the following two methods.

(1) Dehydration Reaction With an Acid Catalyst

The compound (14) is treated in the presence of an acid catalyst such as p-toluenesulfonic acid, sulfuric acid or the like in an inert solvent such as benzene, toluene, xylene or the like at temperatures in the range of room temperature to about reflux temperature of the solvent for about 1 to about 10 hours. If necessary, an excess of an anhydrous inorganic salt such as anhydrous magnesium sulfate, anhydrous sodium sulfate, anhydrous calcium chloride or the like may be added to the reaction system.

(2) Dehydrohalogenation Reaction After Halogenation

The compound (14) is treated with an equivalent amount to a slight equivalent excess of a halogenating agent such as thionyl chloride, thionyl bromide, phosphorus oxychloride or the like in an inert solvent such as dichloromethane, 1,2-dichloroethane, diethyl ether or the like. An equivalent amount to a slight excess of a tertiary amine such as pyridine, lutidine, collidine, triethylamine or the like may be added to the reaction system. The treatment reaction is carried out at temperatures in the range of 0° C. to room temperature for about 5 minutes to about 2 hours.

Subsequently, the compound thus obtained is dehydrohalogenated. The reaction can be carried out in an inert solvent such as benzene, toluene, xylene or the like using about an equimolar amount to an about 3-fold molar amount of a deacidification agent such as 1,8-diazabicyclo[5,4-0]-7-undecene (DBU), triethylamine, N,N-dimethylaniline, 4-(N,N-dimethylamino)pyridine or the like, relative to the starting compound. The reaction is usually carried out at temperatures in the range of 0° C. to room temperature and is completed in about 10 minutes to about 2 hours.

[Reaction Scheme-5]

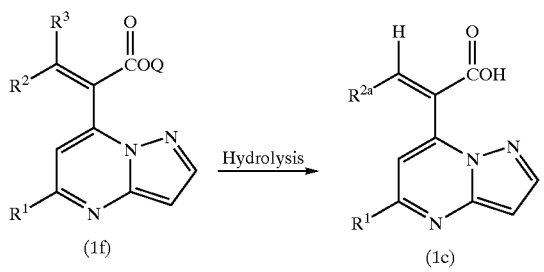

wherein $R^1$, $R^2$, $R^{2a}$, $R^3$ and Q are as defined above.

In Reaction Scheme-5, the compound (1f) is hydrolyzed in an inert solvent such as methanol, ethanol or the like using an aqueous alkali solution such as aqueous sodium hydroxide solution, aqueous potassium hydroxide solution or the like. The aqueous alkali solution is used in an equivalent amount to a slight excess, relative to the compound (1f). The reaction is carried out at temperatures in the range of 0° C. to room temperature and is completed in about 0.5 to about 10 hours.

[Reaction Scheme-6]

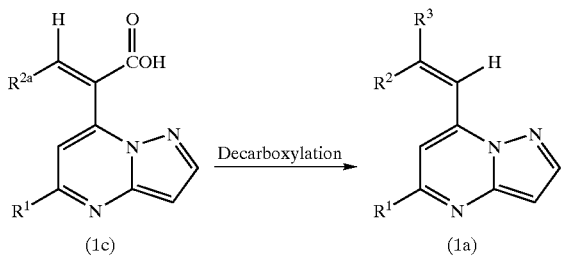

wherein $R^1$, $R^2$, $R^{2a}$, $R^3$ and Q are as defined above.

In Reaction Scheme-6, the compound (1c) is decarboxylated by heating the compound (1c) in an inert solvent such as benzene, toluene, xylene or the like in the presence of an amine such as DBU, triethylamine, N,N-dimethylaniline, 4-(N,N-dimethylamino)pyridine or the like, and a thiol such as thiophenol, ethanethiol or the like at about reflux temperature of the solvent for about 30 minutes to about 5 hours. Both of the amine and thiol are used in a catalytic amount.

[Reaction Scheme-7]

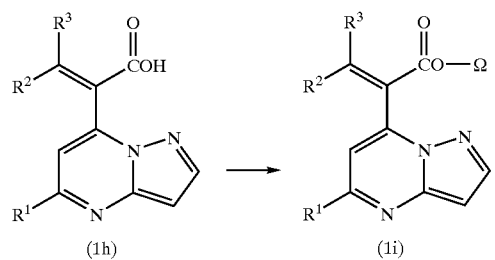

wherein $R^1$, $R^2$ and $R^3$ are as defined above, Ω is lower alkyl, phenylthiomethyl, substituted benzyl having 1 to 3 substituents selected from the group consisting of lower alkoxy, halogen and nitro, or phenyl which may have halogen or nitro as a substituent.

In the above definition, the substituted benzyl having 1 to 3 substituents selected from the group consisting of lower alkoxy, halogen and nitro includes, for example, 2-methoxybenzyl, 3-methoxybenzyl, 4-methoxybenzyl, 3-ethoxybenzyl, 3-propoxybenzyl, 3-butoxybenzyl, 3-pentyloxybenzyl, 3-hexyloxybenzyl, 2-chlorobenzyl, 3-chlorobenzyl, 4-chlorobenzyl, 4-bromobenzyl, 4-iodobenzyl, 4-fluorobenzyl, 2-nitrobenzyl, 3-nitrobenzyl, 4-nitrobenzyl, 2,3-dimethoxybenzyl, 2,4-dimethoxybenzyl, 3,4-dimethoxybenzyl, 3,5-dimethoxybenzyl, 2,3-dichlorobenzyl, 2,4-dichlorobenzyl, 3,4-dichlorobenzyl, 3,5-dichlorobenzyl, 2,4-dinitrobenzyl, 3,5-dinitrobenzyl, 2,3,4-trimethoxybenzyl, 2,3,5-trimethoxybenzyl, 2,3,6-trimethoxybenzyl, 2,4,5-trimethoxybenzyl, 2,4,6-trimethoxybenzyl, 3,4,5-trimethoxybenzyl, 2,4,6-trichlorobenzyl, 2,4,6-trinitrobenzyl and the like.

The phenyl which may have halogen or nitro as a substituent includes 2-chlorophenyl, 3-chlorophenyl, 4-chlorophenyl, 4-bromophenyl, 4-iodophenyl, 4-fluorophenyl, 2-nitrophenyl, 3-nitrophenyl, 4-nitrophenyl and the like.

The conversion reaction of the compound (1h) to compound (1i) shown in Reaction Scheme-7 is carried out, for example, by either of the following two methods.

(1) Reaction With a Halide

The compound (1h) is reacted with a halide of the formula Ω-X (wherein Ω and X are as defined above) in an inert solvent such as DMF, DMA, THF, dichloromethane or the like in the presence of a deacidification agent such as triethylamine, N,N-dimethylaniline, 4-(N,N-dimethylamino)pyridine or the like. Each of the halide and the deacidification agent is used in about an equimolar amount to an about 3-fold molar amount, relative to the compound (1h). The reaction is usually carried out at room temperature to reflux temperature of the solvent for about 30 minutes to about 5 hours.

(2) Reaction With an Oxy Derivative

The compound (1h) is reacted with an oxy derivative of the formula Ω-OH (wherein Ω is as defined above) in an inert solvent such as dichloromethane, 1,2-dichloroethane or the like in the presence of a dehydrating agent such as dicyclohexylcarbodiimide (DCC), diethoxy phosphoryl cyanide (DEPC) or the like. Each of the oxy derivative and the dehydrating agent is used in an equivalent amount to a slight equivalent excess, relative to the compound (1h). The reaction is usually carried out at 0° C. to room temperature and is completed in about 5 hours to about 100 hours.

[Reaction Scheme-8]

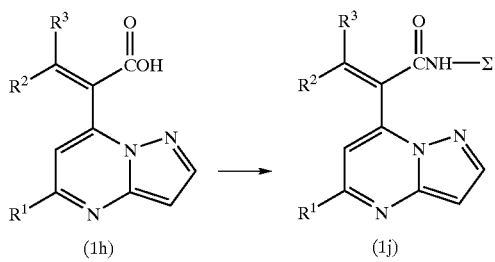

wherein $R^1$, $R^2$ and $R^3$ are as defined above, $\Sigma$ is hydrogen, lower alkyl, benzyl, lower alkoxy-carbonyl-lower alkyl, halophenyl or 1-lower alkoxy-carbonyl-2-phenylethyl.

The lower alkoxy-carbonyl-lower alkyl group represented by $\Sigma$ includes ($C_{1-6}$-alkoxy)carbonyl-($C_{1-6}$-alkyl) groups. The halophenyl group includes a phenyl group having on the phenyl ring, a halogen atom selected from fluorine, chlorine, bromine and iodine. The 1-lower alkoxy-carbonyl-2-phenylethyl group includes 1-($C_{1-6}$-alkoxy)carbonyl-2-phenylethyl.

The conversion reaction of the compound (1h) to a compound (1j) shown in Reaction Scheme-8 is carried out by the following method. The compound (1h) is reacted with a chloroformic acid ester such as isobutyl chloroformate, methyl chloroformate or the like in an inert solvent such as THF, diethyl ether, 1,4-dioxane or the like in the presence of a tertiary amine such as triethylamine, trimethylamine, N,N-dimethylaniline, 4-(N,N-dimethylamino)pyridine or the like to produce a mixed acid anhydride. The mixed acid anhydride is reacted with an amine derivative represented by the formula $\Sigma$-$NH_2$ wherein $\Sigma$ is as defined above. Each of the composition for elimination, tertiary amine and amine derivative is used in an equivalent amount to a slight equivalent excess, relative to the compound (1h). The reaction treatment with the compound for elimination is usually carried out at temperatures in the range of 0° C. to room temperature for about 10 minutes to about 1 hour. The reaction treatment with the amine derivative is usually carried out at temperatures in the range of 0° C. to room temperature for about 30 minutes to about 10 hours. The reactions may be sequentially carried out in the same reactor.

The conversion reaction of the compound (1h) to the compound (1j) shown in Reaction Scheme-8 may also be carried out in accordance with the method (2) of Reaction Scheme-7 (Reaction with an oxy derivative), which comprises reacting the compound (1h) with an amine derivative of $\Sigma$-$NH_2$ (wherein $\Sigma$ is as defined above) in the presence of a dehydrating agent. The amounts of the amine derivative and the dehydrating agent and the reaction conditions may be the same as in the method (2) of Reaction Scheme-7.

[Reaction Scheme-9]

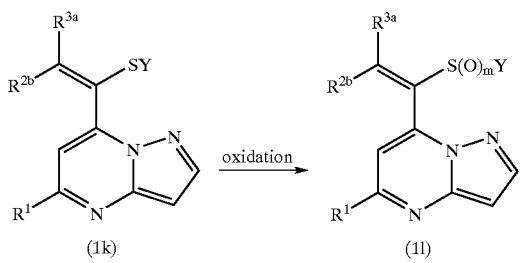

wherein $R^1$ is lower alkyl, thienyl or phenyl; one of $R^{2b}$ and $R^{3a}$ is hydrogen and the other is naphthyl, substituted phenyl having 1 to 3 substituents selected from the group consisting of lower alkoxy, phenyl-lower alkoxy and hydroxyl, or phenyl which may have a substituent selected from the group consisting of N,N-di-lower alkylamino, halogen-substituted lower alkyl, phenyl, nitro, methylenedioxy and halogen.

The oxidation reaction of the compound (1k) shown in Reaction Scheme-9 can be carried out using an oxidizing agent such as hydrogen peroxide, m-chloroperbenzoic acid, sodium periodate or the like in an inert solvent such as acetic acid, dichloromethane, carbon tetrachloride or the like. Using the oxidizing agent in an equivalent amount to a slight equivalent excess relative to the starting compound, a sulfinyl compound (n=1) is obtained by the oxidation reaction at 0° C. to room temperature for about 15 minutes to about 10 hours. To obtain a sulfonyl compound (n=2), the oxidizing agent is used in an amount of 2 equivalents or more relative to the starting compound, optionally using a catalyst such as sodium tungstate or the like, and the reaction is carried out at temperatures in the range of 0° C. to reflux temperature of the solvent for about 15 minutes to about 10 hours.

The desired compound wherein n=2 (sulfonyl compound) can also be produced by oxidizing the compound wherein n=1 (sulfinyl compound) once again in a similar manner. The reaction can be carried out under any of the above-mentioned conditions.

[Reaction Scheme-10]

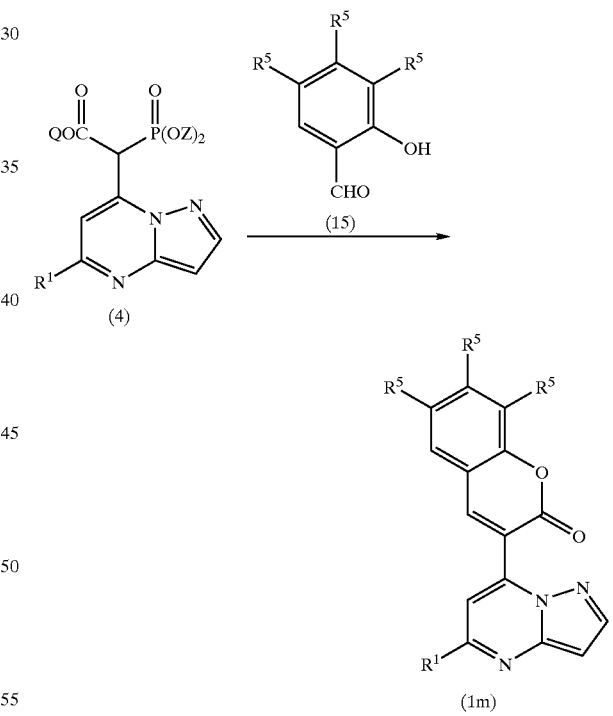

wherein $R^1$, $R^5$, Q and Z are as defined above.

The reaction between the compound (4) and known salicylaldehyde derivative (15) shown in Reaction Scheme-10 can be carried out in a similar manner as in the reaction between the compound (11) and aldehyde derivative (6) shown in Reaction Scheme-3. The solvent and reaction conditions may also be the same as in the reaction between the compound (11) and aldehyde derivative (6). If necessary, an equivalent amount to a slight excess of a crown ether such as 18-crown-6 may be used in the reaction.

[Reaction Scheme-11]

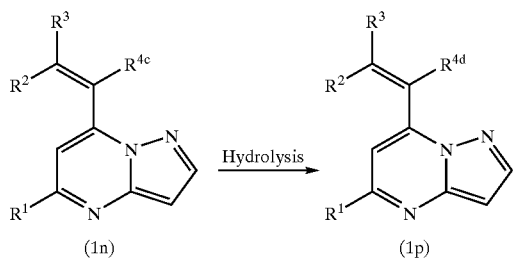

wherein $R^1$, $R^2$ and $R^3$ are as defined above, $R^{4c}$ is N-(lower alkoxy-carbonyl-lower alkyl)carbamoyl or N-(1-lower alkoxy-carbonyl-2-phenylethyl)carbamoyl, and $R^{4d}$ is N-(carboxy-lower alkyl)carbamoyl or N-(1-carboxy-2-phenylethyl)carbamoyl.

According to Reaction Scheme-11, the compound (1n) obtainable by the method shown in Reaction Scheme-8 is hydrolyzed to form a compound (1p). The hydrolysis of the compound (1n) can be carried out in a similar manner as in the hydrolysis of the compound (1f) shown in Reaction Scheme-5, thus giving the compound (1p) having a corresponding hydrolyzed group.

[Reaction Scheme-12]

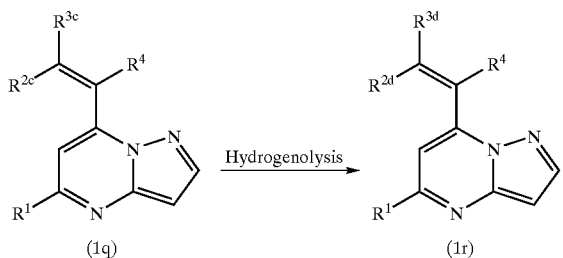

wherein $R^1$ and $R^4$ are as defined above, one of $R^{2c}$ and $R^{3c}$ is hydrogen and the other is substituted phenyl having 1 to 3 benzyloxy groups and optionally further having 1 to 2 lower alkoxy groups, $R^{2d}$ and $R^{3d}$ correspond to $R^{2c}$ and $R^{3c}$ and one of $R^{2d}$ and $R^{3d}$ is a substituted phenyl group having hydroxyl groups in place of benzyloxy groups (i.e., substituted phenyl having 1 to 3 hydroxyl groups and optionally further having 1 to 2 lower alkoxy groups).

As shown in Reaction Scheme-12, the compound (1q) having benzyloxy-substituted phenyl is hydrogenolized to convert benzyloxy groups into hydroxyl groups. The reaction can be carried out in an inert solvent such as ethanol, methanol, ethyl acetate or the like in the presence of a catalytic amount of a catalyst such as palladium-carbon, platinum oxide, Raney nickel or the like in an atmosphere of hydrogen in a stoichiometric amount or more at temperatures in the range of 0° C. to room temperature. The reaction is completed in about 5 minutes to about 1 hour, thus giving a compound (1r).

In the above reaction, it is preferable to promptly stop the reaction upon consumption of a stoichiometric amount of hydrogen so that double bonds of carbon atoms bound to $R^{2c}$ and $R^{3c}$ of the starting compound may not be hydrogenated.

The compounds obtained by the processes shown in the above Reaction Schemes can be easily isolated by conventional separation and purification methods. Examples of such methods include adsorption chromatography, preparative thin-layer chromatography, recrystallization, solvent extraction and the like.

The compounds of the invention can be formed into pharmaceutically acceptable acid addition salts. The compounds of the invention include such salts. Acids for use to form such acid addition salts are, for example, inorganic acids such as hydrochloric acid, hydrobromic acid, sulfuric acid and the like and organic acids such as oxalic acid, fumaric acid, maleic acid, tartaric acid, citric acid, p-toluenesulfonic acid and the like. These acid addition salts can be formed according to conventional methods.

The compounds of the invention can be formed into alkali metal salts such as sodium salts, potassium salts or the like, alkaline earth metal salts such as calcium salts, magnesium salts or the like and other salts such as copper salts or the like, by conventional methods. Such salts also constitute part of the compounds of the invention.

Some of the compounds of the invention exist as optical isomers having a carbon atom as an asymmetric center. Optical isomers in the form of R-body, S-body and racemic body are included among the compounds of the invention.

For use, the compounds of the invention are usually shaped into general dosage forms for pharmaceutical compositions with pharmaceutically acceptable carriers. Examples of pharmaceutically acceptable carriers include conventional diluents or excipients such as fillers, volume builders, binders, humectants, disintegrators, surfactants, lubricants and the like. These carriers are selectively used according to the desired unit dosage form.

The unit dosage form for the pharmaceutical compositions of the invention can be selected from a broad variety of forms according to the intended medical treatment. Typical examples are tablets, pills, powders, solutions, suspensions, emulsions, granules, capsules, suppositories, injections (solutions, suspensions, etc.), ointments, and the like.

For preparing tablets by molding, usable as the above pharmaceutically acceptable carriers are excipients such as lactose, sucrose, sodium chloride, glucose, urea, starch, calcium carbonate, kaolin, crystalline cellulose, silicic acid and potassium phosphate; binders such as water, ethanol, propanol, simple syrup, glucose syrup, starch solution, gelatin solution, carboxymethyl cellulose, hydroxypropyl cellulose, methyl cellulose and polyvinyl pyrrolidone; disintegrators such as sodium carboxymethyl cellulose, calcium carboxymethyl cellulose, low-substituted hydroxypropyl cellulose, dry starch, sodium alginate, agar powder, laminaran powder, sodium hydrogen-carbonate and calcium carbonate; surfactants such as polyoxyethylene sorbitan fatty acid esters, sodium lauryl sulfate and stearyl monoglyceride; disintegration inhibitors such as sucrose, stearin, cacao butter and hydrogenated oil; absorption promoters such as quaternary ammonium base and sodium lauryl sulfate; humectants such as glycerin and starch; adsorbents such as starch, lactose, kaolin, bentonite and colloidal silicic acid; and lubricants such as purified talc, stearic acid salt, boric acid powder and polyethylene glycol.

The tablets may further be made into coated tablets such as sugar-coated tablets, gelatin-coated tablets, enteric tablets, film-coated tablets, double-layered tablets or multiple-layered tablets.

For preparing pills by molding, usable as pharmaceutically acceptable carriers are excipients such as glucose, lactose, starch, cacao butter, hydrogenated vegetable oil, kaolin and talc; binders such as gum arabic powder, tragacanth powder, gelatin and ethanol; and disintegrators such as laminaran and agar.

For formulating suppositories, usable as pharmaceutically acceptable carriers are polyethylene glycol, cacao butter, a higher alcohol or its esters, gelatin, semisynthetic glycerides and the like. The capsules are usually manufactured in a conventional manner by blending the compound of the invention with one or more pharmaceutically acceptable carriers as exemplified above and encapsulating the mixture into hard gelatin capsule shells, soft capsule shells, etc.

When the pharmaceutical preparation is to be provided in an injectable form such as a solution, an emulsion or a suspension, the preparation is preferably sterilized and rendered isotonic to the blood. Diluents for use in such preparation are, for example, water, ethanol, macrogols, propylene glycol, ethoxylated isostearyl alcohol, polyoxyisostearyl alcohol, polyoxyethylene sorbitan fatty acid esters and the like. In this case, sodium chloride, glucose or glycerin may be added to the pharmaceutical composition in an amount sufficient to provide an isotonic solution. Conventional solubilizers, buffers, anesthetics and the like may also be added to the pharmaceutical composition.

Further, if desired, coloring agents, preservatives, aromatics, flavors, sweeteners or other medicines may be incorporated into the pharmaceutical composition.

For preparing ointments in the form of pastes, creams, gels, etc., usable as diluents are white petrolatum, paraffin, glycerin, cellulose derivatives, polyethylene glycol, silicone, bentonite and the like.

The present inventors found that when a pyrazolo[1,5-a]pyrimidine derivative of formula (1) wherein $R^4$ is carboxyl is used as an active ingredient and mixed with a suitable acid polymer, oral administration of the resulting mixture (composition) improves permeability of the active ingredient through the intestinal membrane. Examples of useful acid polymers are aqueous solutions and suspensions of acid polymers at or below pH 6. Specific examples include hydroxypropyl methylcellulose phthalate, hydroxymethylcellulose acetate succinate, methacrylic acid/methacrylate copolymers and the like. Particularly preferred are methacrylic acid/methacrylate copolymers (1:1) (e.g., trade name: Eudragit L100, product of Rohm Pharm. Co., Ltd.)

The proportion of the compound of the formula (1) of the invention (active ingredient) in the pharmaceutical preparation is not critical and can be selected from a broad range. It is usually preferable for the compound to account for about 1 to about 70 wt. % of the pharmaceutical preparation.

There is no limitation on the method for administering the pharmaceutical preparation. A proper method can be selected according to the dosage form, patient's age, sex and other conditions, severity of disease, etc. For example, the tablets, pills, solutions, suspensions, emulsions, granules and capsules are administered by the oral route. The injections are administered singly or in admixture with glucose, amino acid or like conventional infusions by the intravenous route or if necessary, administered singly by the intramuscular, intradermal, subcutaneous or intraperitoneal route. The suppositories are administered intrarectally.

The dosage of the pharmaceutical preparation is suitably selected according to the intended use, patient's age, sex and other conditions, severity of disease, etc. The dosage of the compound of the invention as the active ingredient is preferably about 0.5 to about 20 mg per kg body weight a day for human adult. The pharmaceutical preparation may be administered once a day or in 2–4 divided doses a day.

BEST MODE FOR CARRYING OUT THE INVENTION

Given below are Examples illustrating the production processes for the compounds of the invention. Reference Examples illustrate preparation processes for the starting compounds (or intermediates) for preparing the compounds of the invention.

REFERENCE EXAMPLE 1

12.0 g of 60% sodium hydride was added to 100 ml of DMF, followed by cooling to 0° C. Thereto was added 70.6 g of triethyl phosphonoacetate, followed by stirring at 0° C. for 1 hour and further stirring at room temperature for 4 hours. The mixture was cooled to 0° C. again and a solution of 30 g of 5-n-butyl-7-chloropyrazolo[1,5-a]pyrimidine in 20 ml of DMF was added dropwise, followed by stirring at 0° C. for 30 minutes and further stirring at room temperature for 65 hours. The reaction mixture was poured into 2 l of ice water. The aqueous layer was washed twice with 600 ml of n-hexane and extracted with 100 ml of 5% aqueous sodium hydroxide solution. Then 300 ml of ethyl acetate and 42 g of citric acid were added to the extract and stirred at room temperature for 30 minutes, followed by extraction with ethyl acetate. The organic layer was washed with water, dried over anhydrous magnesium sulfate and concentrated under reduced pressure. The residue was purified by silica gel column chromatography (eluent; ethyl acetate:n-hexane=1:1). As a result, 41 g of (5-n-butylpyrazolo[1,5-a]pyrimidin-7-yl)triethyl phosphonoacetate was obtained as an oily product.

The following compounds were prepared in a similar manner as above.

(5-Methylpyrazolo[1,5-a]pyrimidin-7-yl)triethyl phosphonoacetate (5-Ethylpyrazolo[1,5-a]pyrimidin-7-yl)triethyl phosphonoacetate (5-n-Propylpyrazolo[1,5-a]pyrimidin-7-yl)triethyl phosphonoacetate (5-n-Pentylpyrazolo[1,5-a]pyrimidin-7-yl)triethyl phosphonoacetate (5-n-Hexylpyrazolo[1,5-a]pyrimidin-7-yl)triethyl phosphonoacetate

[5-(2-Thienyl)pyrazolo[1,5-a]pyrimidin-7-yl]triethyl phosphonoacetate

[5-(3-Thienyl)pyrazolo[1,5-a]pyrimidin-7-yl]triethyl phosphonoacetate (5-Phenylpyrazolo[1,5-a]pyrimidin-7-yl)triethyl phosphonoacetate.

REFERENCE EXAMPLE 2

50 ml of 2% aqueous sodium hydroxide solution was added to 5 g of (5-n-butylpyrazolo[1,5-a]pyrimidin-7-yl)

triethyl phosphonoacetate obtained in Reference Example 1, followed by stirring at 60° C. for 1.5 hours. After addition of ice water, the reaction mixture was neutralized with 1.75 g of citric acid and extracted with chloroform. The organic layer was collected, washed sequentially with water and saturated aqueous sodium chloride solution and concentrated under reduced pressure. The residue was purified by silica gel column chromatography (eluent; ethyl acetate:n-hexane=1:2→2:1). As a result, 2.6 g of diethyl (5-n-butylpyrazolo-[1,5-a]pyrimidin-7-yl)methylphosphonate was obtained as an oily product.

The following compounds were prepared in a similar manner as above.

Diethyl (5-methylpyrazolo[1,5-a]pyrimidin-7-yl) methylphosphonate
Diethyl (5-ethylpyrazolo[1,5-a]pyrimidin-7-yl) methylphosphonate
Diethyl (5-n-propylpyrazolo[1,5-a]pyrimidin-7-yl) methylphosphonate
Diethyl (5-n-pentylpyrazolo[1,5-a]pyrimidin-7-yl) methylphosphonate
Diethyl (5-n-hexylpyrazolo[1,5-a]pyrimidin-7-yl) methylphosphonate
Diethyl [5-(2-thienyl)pyrazolo[1,5-a]pyrimldin-7-yl] methylphosphonate
Diethyl [5-(3-thienyl)pyrazolo[1,5-a]pyrimidin-7-yl] methylphosphonate
Diethyl (5-phenylpyrazolo[1,5-a]pyrimidin-7-yl) methylphosphonate.

Example 1
Preparation of (E)-5-n-butyl-7-[2-(3,4,5-trimethoxyphenyl)ethenyl]pyrazolo[1,5-a]pyrimidine 1.0 g of diethyl (5-n-butylpyrazolo[1,5-a]pyrimidin-7-yl)methylphosphonate obtained in Reference Example 2 and 0.66 g of 3,4,5-trimethoxybenzaldehyde were dissolved in 5.0 ml of ethanol, followed by cooling to 0° C. Thereto was added 3.8 ml of 5% aqueous potassium hydroxide solution, followed by stirring at 0° C. for 1 hour. After completion of the reaction, the crystals precipitated were collected and washed with 10% aqueous ethanol solution and recrystallized from ethanol. 0.72 g of the desired compound was obtained as crystals. The structure and melting point of the compound obtained are shown in Table 1.

Examples 2–7

The compounds shown in Table 1 were prepared in a similar manner as in Example 1.

Examples 8–9
Preparation of (E)-5-n-butyl-7-[2-(4-chlorophenyl)ethenyl]pyrazolo[1,5-a]pyrimidine and (Z)-5-n-butyl-7-[2-(4-chlorophenyl)ethenyl]pyrazolo[1,5-a]pyrimidine Using diethyl (5-n-butylpyrazolo[1,5-a]pyrimidin-7-yl)methylphosphonate obtained in Reference Example 2 and 4-chlorobenzaldehyde, a reaction was carried out in a similar manner as in Example 1 and the crude product was recrystallized from ethanol-water, thus giving an E compound (pure product). Subsequently, mother liquor was extracted with ethyl acetate, washed with water and concentrated under reduced pressure. The residue was purified by silica gel column chromatography (eluent; ethyl acetate:n-hexane=1:4), thus giving a Z compound (pure product, a colorless oily product). The structure and melting point of the compounds obtained are shown in Table 1.

Examples 10 and 11

The compounds shown in Table 1 were prepared in a similar manner as in Examples 8 and 9.

REFERENCE EXAMPLE 3

30.7 ml of n-butyl lithium (1.63 M, n-hexane solution) was diluted with 35 ml of THF, and the diluted solution was cooled to −78° C. in an atmosphere of argon. Thereto was added a solution of 10.4 g of diethyl methylthiomethylphosphonate in 10 ml of THF, followed by stirring at −78° C. for 1 hour. Thereto was added dropwise a solution of 5 g of 5-n-butyl-7-chloropyrazolo[1,5-a]pyrimidine in 5 ml of THF, followed by stirring at −78° C. for 1 hour. The reaction mixture was diluted with ethyl acetate and washed sequentially with aqueous ammonium chloride solution, water and saturated saline and concentrated under reduced pressure. The residue was purified by silica gel column chromatography (eluent; ethyl acetate:n-hexane=1:3→1:1). As a result, 5.9 g of diethyl (5-n-butylpyrazolo[1,5-a]pyrimidin-7-yl)methylthiomethylphosphonate was obtained as an oily product.

The following compounds were prepared in a similar manner as above.

Diethyl (5-methylpyrazolo[1,5-a]pyrimidin-7-yl) methylthiomethylphosphonate
Diethyl (5-ethylpyrazolo[1,5-a]pyrimidin-7-yl) methylthiomethylphosphonate
Diethyl (5-n-propylpyrazolo[1,5-a]pyrimidin-7-yl) methylthiomethylphosphonate
Diethyl (5-n-pentylpyrazolo[1,5-a]pyrimidin-7-yl) methylthiomethylphosphonate
Diethyl (5-n-hexylpyrazolo[1,5-a]pyrimidin-7-yl) methylthiomethylphosphonate
Diethyl [5-(2-thienyl)pyrazolo[1,5-a]pyrimidin-7-yl] methylthiomethylphosphonate
Diethyl [5-(3-thienyl)pyrazolo[1,5-a]pyrimidin-7-yl] methylthiomethylphosphonate
Diethyl (5-phenylpyrazoro[1,5-a]pyrimidin-7-yl) methylthiomethylphosphonate
Diethyl (5-n-butylpyrazolo[1,5-a]pyrimidin-7-yl) ethylthiomethylphosphonate
Diethyl (5-n-butylpyrazolo[1,5-a]pyrimidin-7-yl)-n-propylthiomethylphosphonate
Diethyl (5-n-butylpyrazolo[1,5-a]pyrimidin-7-yl)-n-butylthiomethylphosphonate
Diethyl (5-n-butylpyrazolo[1,5-a]pyrimidin-7-yl)-n-pentylthiomethylphosphonate
Diethyl (5-n-butylpyrazolo[1,5-a]pyrimidin-7-yl)-n-hexylthiomethylphosphonate.

Example 12
Preparation of (Z)-5-n-butyl-7-[1-methylthio-2-(3,4,5-trimethoxyphenyl)ethenyl]pyrazolo[1,5-a]pyrimidine 5.5 g of diethyl (5-n-butylpyrazolo[1,5-a]pyrimidin-7-yl)methylthiomethylphosphonate obtained in Reference Example 3 was dissolved in 25 ml of dimethoxyethane, followed by cooling to 0° C. Thereto was added 2.0 g of potassium-t-butoxide, followed by cooling to 0° C. Then 3.2 g of 3,4,5-trimethoxybenzaldehyde was added, followed by stirring at room temperature for 15 minutes and further stirring at 60° C. for 3 hours. After completion of the reaction, the reaction mixture was concentrated under reduced pressure. The residue was diluted with ethyl acetate, washed sequentially with water and with saturated saline and concentrated under reduced pressure. The residue obtained was purified by silica gel column chromatography (eluent; ethyl acetate:n-hexane=1:2) and recrystallized from diethyl ether-n-hexane. 1.7 g of the desired compound was obtained as crystals. The structure and melting point of the compound obtained are shown in Table 1.

Examples 13–26

The compounds shown in Table 1 were prepared in a similar manner as in Example 12, using the compounds obtained in Reference Example 1 as starting compounds.

REFERENCE EXAMPLE 4

Using diethyl ethylphosphonate and 5-n-butyl-7-chloropyrazolo[1,5-a]pyrimidine, the procedure was carried out in a similar manner as in Reference Example 3, thus giving diethyl 1-(5-n-butylpyrazolo[1,5-a]pyrimidin-7-yl) ethylphosphonate.

The following compounds were prepared in a similar manner as above.
Diethyl 1-(5-methylpyrazolo[1,5-a]pyrimidin-7-yl) ethylphosphonate
Diethyl 1-(5-ethylpyrazolo[1,5-a]pyrimidin-7-yl) ethylphosphonate
Diethyl 1-(5-n-propylpyrazolo[1,5-a]pyrimidin-7-yl) ethylphosphonate
Diethyl 1-(5-n-pentylpyrazolo[1,5-a]pyrimidin-7-yl) ethylphosphonate
Diethyl 1-(5-n-hexylpyrazolo[1,5-a]pyrimidin-7-yl) ethylphosphonate
Diethyl 1-[5-(2-thienyl)pyrazolo[1,5-a]pyrimidin-7-yl] ethylphosphonate
Diethyl 1-[5-(3-thienyl)pyrazolo[1,5-a]pyrimidin-7-yl] ethylphosphonate
Diethyl 1-(5-phenylpyrazoro[1,5-a]pyrimidin-7-yl) ethylphosphonate
Diethyl 1-(5-n-butylpyrazolo[1,5-a]pyrimidin-7-yl) propylphosphonate
Diethyl 1-(5-n-butylpyrazolo[1,5-a]pyrimidin-7-yl) butylphosphonate
Diethyl 1-(5-n-butylpyrazolo[1,5-a]pyrimidin-7-yl) pentylphosphonate
Diethyl 1-(5-n-butylpyrazolo[1,5-a]pyrimidin-7-yl) hexylphosphonate
Diethyl 1-(5-n-butylpyrazolo[1,5-a]pyrimidin-7-yl) heptylphosphonate.

Example 27
Preparation of (E)-5-n-butyl-7-[1-(3,4,5-trimethoxyphenyl) propen-2-yl]pyrazolo[1,5-a]pyrimidine Using diethyl 1-(5-n-butylpyrazolo[1,5-a]pyrimidin-7-yl) ethylphosphonate as a starting compound, the procedure was carried out in a same manner as in Example 12, thus giving the compound shown in Table 1.

Examples 28–29
Preparation of (E)-ethyl 2-(5-n-butylpyrazolo[1,5-a] pyrimidin-7-yl)-3-(4-chlorophenyl)acrylate and (Z)-ethyl 2-(5-n-butylpyrazolo[1,5-a]pyrimidin-7-yl)-3-(4-chlorophenyl)acrylate Using (5-n-butylpyrazolo[1,5-a]pyrimidin-7-yl)triethyl phosphonoacetate obtained in Reference Example 1 and 4-chlorobenzaldehyde, a reaction was carried out in the same manner as in Example 12. The crude product obtained was purified by silica gel column chromatography (eluent; ethyl acetate:n-hexane=1:10→1:3), whereby a Z compound was obtained from the former fraction and an E compound was obtained from the latter fraction. The structure and melting point of the compounds obtained are shown in Table 1.

Examples 30–39

The compounds shown in Table 1 were prepared in a similar manner as in Examples 28 and 29.

Example 40
Preparation of (E) 2-(5-n-butylpyrazolo[1,5-a]pyrimidin-7-yl)-3-(3,4,5-trimethoxyphenyl)acrylic Acid 18.0 g of the compound obtained in Example 31 was dissolved in 180 ml of ethanol. Then 36 ml of 5% aqueous sodium hydroxide solution was added, followed by stirring at room temperature for 4 hours. The reaction mixture was concentrated under reduced pressure and then acidified by addition of water and 6.38 g of citric acid, followed by extraction with ethyl acetate. The organic layer was collected, washed sequentially with water and with saturated saline and concentrated under reduced pressure. The residue was recrystallized from ethyl acetate-n-hexane at room temperature. As a result, 13.65 g of the desired compound having a melting point of 117–120° C. (decomposition) was obtained as crystals.

The crystals thus obtained were dissolved in ethyl acetate. While heating the solution in a hot bath, n-hexane was gradually added, whereby crystals were precipitated. The crystals had a melting point of 153° C. or higher (decomposition) and had the same structure as the above compound.

The structure and melting point of the compound obtained are shown in Table 1.

The compound obtained in Example 30 was hydrolyzed in a similar manner as above. The same compound as above was obtained.

Examples 41–59

The compounds shown in Table 1 were prepared in a similar manner as in Example 40.

Example 60
Preparation of (E)-5-n-butyl-7-[2-(4-methylthiophenyl)-ethenyl]pyrazolo[1,5-a]pyrimidine 0.50 g of the compound obtained in Example 44 was dissolved in 10 ml of toluene, followed by adding 0.1 ml of thiophenol and 0.1 ml of DBU. The mixture was refluxed for 1 hour. The reaction mixture was allowed to cool, diluted with ethyl acetate, washed sequentially with water and with saturated saline and concentrated under reduced pressure. The residue was recrystallized from n-hexane. 0.28 g of the desired compound was obtained as crystals. The structure and melting point of the compound obtained are shown in Table 1.

Examples 61–69

The compounds shown in Table 1 were prepared in a similar manner as in Example 60.

Example 70
Preparation of (E)-ethyl 2-(5-n-butylpyrazolo[1,5-a]pyrimidin-7-yl)-3-(3,4,5-trimethoxyphenyl)acrylate 2.0 g of the compound obtained in Example 40 was dissolved in 10 ml of DMF. To the solution were added 1.0 ml of triethylamine and 0.78 ml of ethyl iodide, followed by stirring at 60° C. for 2 hours. After completion of the reaction, the reaction mixture was concentrated under reduced pressure. The residual crystals were separated from the concentrate by filtration and washed with diethyl ether. The filtrate and washing fluid were washed sequentially with water and with saturated saline and concentrated under reduced pressure. The residue was purified by silica gel column chromatography (eluent; ethyl acetate:n-hexane= 1:4→1:1) and recrystallized from diethyl ether-n-hexane. 1.55 g of the desired compound (the same compound as in Example 31) was obtained as crystals.

Examples 71–75

The compounds shown in Table 1 were prepared in a similar manner as in Example 70.

Example 76
Preparation of (E)-2-(5-n-butylpyrazolo[1,5-a]pyrimidin-7-yl)-4-chlorophenyl-3-(3,4,5-trimethoxyphenyl)acrylate 0.50 g of the compound obtained in Example 40 and 0.16 g of 4-chlorophenol were dissolved in 4 ml of dichloromethane, followed by cooling to 0° C. Thereto was added 1 ml of dichloromethane solution containing 0.25 g of DCC, followed by stirring at 0° C. for 1 hour and at room temperature for 60 hours. After completion of the reaction, the reaction mixture was diluted with ethyl acetate and the insoluble material was separated by filtration. The filtrate was washed sequentially with aqueous sodium hydroxide solution, water and saturated saline and concentrated under reduced pressure. The residue was purified by silica gel column chromatography (eluent; ethyl acetate:n-hexane= 1:4→1:2) and recrystallized from diethyl ether-n-hexane. 0.48 g of the desired compound was obtained as crystals. The structure and melting point of the compound obtained are shown in Table 1.

Examples 77–79

The compounds shown in Table 1 were prepared in a similar manner as in Example 76.

Example 80
Preparation of (E)-2-(5-n-butylpyrazolo[1,5-a]pyrimidin-7-yl)-N-ethyl-3-(3,4,5-trimethoxyphenyl)acrylamide 0.70 g of the compound obtained in Example 40 was dissolved in 5 ml of THF, followed by cooling to 0° C. Thereto were added 0.28 ml of triethylamine and 0.24 ml of isobutyl chloroformate, followed by stirring at 0° C. for 30 minutes. A solution prepared by diluting 0.94 ml of THF solution of 2M ethylamine with 2 ml of THF was added at 0° C., followed by stirring at 0° C. for 1 hour and at room temperature for 2 hours. After completion of the reaction, the reaction mixture was diluted with ethyl acetate, washed sequentially with water and with saturated saline and concentrated under reduced pressure. The residual crude crystals were recrystallized from ethyl acetate-n-hexane. 0.62 g of the desired compound was obtained as crystals. The structure and melting point of the compound obtained are shown in Table 1.

Examples 81–87

The compounds shown in Table 1 were prepared in a similar manner as in Example 80.

Example 88
Preparation of (Z)-5-n-butyl-7-[1-methylsulfinyl-2-(3,4,5-trimethoxyphenyl)ethenyl]pyrazolo[1,5-a]pyrimidine 0.50 g of the compound obtained in Example 12 was dissolved in 5 ml of acetic acid. To the solution was added 0.14 ml of 30% aqueous hydrogen peroxide solution, followed by stirring at room temperature for 4 hours. The reaction mixture was diluted with dichloromethane, washed sequentially with water, sodium bicarbonate solution and saturated saline and concentrated under reduced pressure. The residue was purified by silica gel column chromatography (eluent; ethyl acetate:n-hexane=1:1→ethyl acetate→dichloroethane:methanol=10:1) and recrystallized from ethyl acetate-n-hexane. 0.38 g of the desired compound was obtained as crystals. The structure and melting point of the compound obtained are shown in Table 1.

Example 89
Preparation of (E)-5-n-butyl-7-[1-methylsulfonyl-2-(3,4,5-trimethoxyphenyl)ethenyl]pyrazolo[1,5-a]pyrimidine 0.50 g of the compound obtained in Example 12 was dissolved in 3 ml of acetic acid. To the solution was added 0.34 ml of aqueous 30% hydrogen peroxide solution, followed by stirring at 60° C. for 4 hours. The reaction mixture was diluted with dichloromethane, washed sequentially with sodium bicarbonate solution, water and saturated saline and concentrated under reduced pressure. The residue was purified by silica gel column chromatography (eluent; ethyl acetate:n-hexane=2:3) and recrystallized from ethyl acetate-n-hexane. 0.24 g of the desired compound was obtained as crystals. The structure and melting point of the compound obtained are shown in Table 1.

Example 90
Preparation of 5-n-butyl-7-(6,7,8-trimethoxycoumarin-3-yl)pyrazolo[1,5-a]pyrimidine 0.21 g of 3,4,5-trimethoxysalicylaldehyde was dissolved in 3 ml of THF. To the solution was added 0.12 g of potassium-t-butoxide, followed by stirring at room temperature for 10 minutes. Thereto was added 2 ml of THF solution containing 0.35 g of (5-n-butylpyrazolo[1,5-a]pyrimidin-7-yl)triethyl phosphonoacetate obtained in Reference Example 1, followed by stirring at room temperature for 10 minutes. Then 0.28 g of 18-crown-6 was added, followed by stirring at room temperature for 120 hours. The reaction mixture was diluted with ethyl acetate, washed sequentially with water and with saturated saline and concentrated under reduced pressure. The residue was purified by silica gel column chromatography (eluent; ethyl acetate:n-hexane=1:2) and recrystallized from ethyl acetate-n-hexane. 0.14 g of the desired compound was obtained as crystals. The structure and melting point of the compound obtained are shown in Table 1.

Example 91

The compound shown in Table 1 was prepared in a similar manner as in Example 90.

TABLE 1
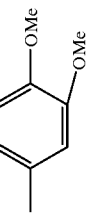
Me = methyl, Et = ethyl, i-Pr = isopropyl, n-Bu = n-butyl, Ph = phenyl
| Example No. | R¹ | R² | R³ | R⁴ | Melting point (° C.) (Recrystalization solvent) |
|---|---|---|---|---|---|
| 1 | n-Bu | H | 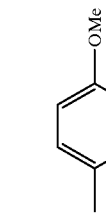 | H | 83~85 (Ethanol-n-hexane) |
| 2 | n-Bu | H | Ph | H | 74~76 (Ethanol-water) |
| 3 | n-Bu | H |  | H | 69~71 (Ethanol-water) |
| 4 | n-Bu | H | 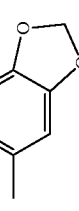 | H | 116~118 (Ethanol-water) |
| 5 | n-Bu | H | 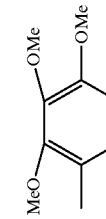 | H | 67~69 (Ethyl acetate-n-hexane) |
| 6 | n-Bu | H | 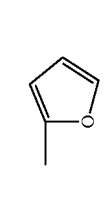 | H | 55~57 (Ethanol-water) |

TABLE 1-continued

Me = methyl, Et = ethyl, i-Pr = isopropyl, n-Bu = n-butyl, Ph = phenyl

| Example No. | $R^1$ | $R^2$ | $R^3$ | $R^4$ | Melting point (° C.) (Recrystalization solvent) |
|---|---|---|---|---|---|
| 7 | n-Bu | H | 4-NMe$_2$-C$_6$H$_4$-Me | H | 131~133 (Ethyl acetate-n-hexane) |
| 8 | n-Bu | H | 4-Cl-C$_6$H$_4$-Me | H | 92~94 (Ethanol-water) |
| 9 | n-Bu | 4-Cl-C$_6$H$_4$- | H | H | Oily product (NMR 1) |
| 10 | n-Bu | H | 2-pyridyl-Me | H | 67~69 (Ethanol-water) |
| 11 | n-Bu | 2-pyridyl-Me | H | H | 62~64 (Ethanol-water) |
| 12 | n-Bu | H | 3,4,5-(OMe)$_3$-C$_6$H$_2$-Me | —SMe | 71~73 (n-Hexane) |
| 13 | n-Bu | Ph | H | —COOEt | Oily product (NMR 2) |

TABLE 1-continued

Me = methyl, Et = ethyl, i-Pr = isopropyl, n-Bu = n-butyl, Ph = phenyl

| Example No. | $R^1$ | $R^2$ | $R^3$ | $R^4$ | Melting point (° C.) (Recrystalization solvent) |
|---|---|---|---|---|---|
| 14 | n-Bu | 4-MeO-C6H4 | H | —COOEt | Oily product (NMR 3) |
| 15 | n-Bu | 4-MeS-C6H4 | H | —COOEt | Oily product (NMR 4) |
| 16 | n-Bu | 4-Me2N-C6H4 | H | —COOEt | Oily product (NMR 5) |
| 17 | n-Bu | 4-CF3-C6H4 | H | —COOEt | Oily product (NMR 6) |
| 18 | n-Bu | 3,4-methylenedioxyphenyl | H | —COOEt | Oily product (NMR 7) |
| 19 | n-Bu | 2,3-dimethoxyphenyl | H | —COOEt | Oily product (NMR 8) |

TABLE 1-continued
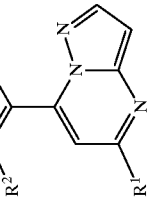
Me = methyl, Et = ethyl, i-Pr = isopropyl, n-Bu = n-butyl, Ph = phenyl
| Example No. | $R^1$ | $R^2$ | $R^3$ | $R^4$ | Melting point (° C.) (Recrystalization solvent) |
|---|---|---|---|---|---|
| 20 | n-Bu | 2-naphthyl | H | —COOEt | Oily product (NMR 9) |
| 21 | n-Bu | 2-furyl | H | —COOEt | Oily product (NMR 10) |
| 22 | Ph | 3,4,5-trimethoxyphenyl | H | —COOEt | Oily product (NMR 11) |
| 23 | n-Bu | 4-fluorophenyl | H | —COOEt | 78~80 (Ethanol-water) |
| 24 | n-Bu | 4-biphenyl | H | —COOEt | 106~108 (Ethanol-water) |

TABLE 1-continued
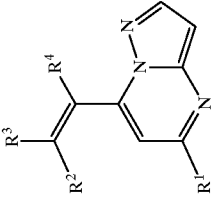
Me = methyl, Et = ethyl, i-Pr = isopropyl, n-Bu = n-butyl, Ph = phenyl
| Example No. | R¹ | R² | R³ | R⁴ | Melting point (° C.) (Recrystalization solvent) |
|---|---|---|---|---|---|
| 25 | n-Bu | 2-Me-4-OMe-phenyl | H | —COOEt | Oily product (NMR 12) |
| 26 | n-Bu | 3-OMe-4-OMe-phenyl (alt: 4-Me-2-OMe) | H | —COOEt | Oily product (NMR 13) |
| 27 | n-Bu | H | 3,4,5-tri-OMe-phenyl | —Me | 122–124(Hydrochloride) (Ethyl acetate) |
| 28 | n-Bu | H | 4-Cl-phenyl | —COOEt | Oily product (NMR 14) |
| 29 | n-Bu | 4-Cl-phenyl | H | —COOEt | Oily product (NMR 15) |

TABLE 1-continued
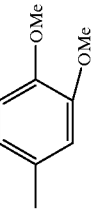
Me = methyl, Et = ethyl, i-Pr = isopropyl, n-Bu = n-butyl, Ph = phenyl
| Example No. | R¹ | R² | R³ | R⁴ | Melting point (° C.) (Recrystalization solvent) |
|---|---|---|---|---|---|
| 30 | n-Bu | H |  | —COOEt | Oily product (NMR 16) |
| 31 | n-Bu | 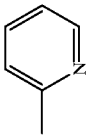 | H | —COOEt | 50–52 (n-Hexane) |
| 32 | n-Bu | 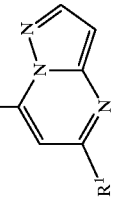 | 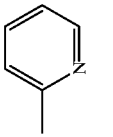 | —COOEt | 72–75 (n-Hexane) |
| 33 | n-Bu | H | 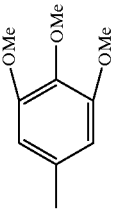 | —COOEt | Oily product (NMR 17) |
| 34 |  | H | 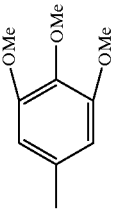 | —COOEt | 166–168 (Ethyl acetate-n-hexane) |

TABLE 1-continued

Me = methyl, Et = ethyl, i-Pr = isopropyl, n-Bu = n-butyl, Ph = phenyl

| Example No. | R¹ | R² | R³ | R⁴ | Melting point (°C) (Recrystalization solvent) |
|---|---|---|---|---|---|
| 35 | 5-methyl-2-thienyl | 3,4,5-trimethoxyphenyl (with 4-Me) | H | —COOEt | Oily product (NMR 18) |
| 36 | n-Bu | H | 4-nitrophenyl | —COOEt | 96–98 (ethyl acetate-n-hexane) |
| 37 | n-Bu | 4-nitrophenyl | H | —COOEt | 116–118 (Ethyl acetate-n-hexane) |
| 38 | n-Bu | H | (1-phenylpropenyl) | —COOEt | 118–120 (n-Hexane) |
| 39 | n-Bu | (1-phenylpropenyl) | H | —COOEt | 103–105 (Ethyl acetate-n-hexane) |

TABLE 1-continued

Me = methyl, Et = ethyl, i-Pr = isopropyl, n-Bu = n-butyl, Ph = phenyl

| Example No. | R¹ | R² | R³ | R⁴ | Melting point (° C.) (Recrystalization solvent) |
|---|---|---|---|---|---|
| 40 | n-Bu | 3,4,5-tri(OMe)-phenyl | H | —COOH | 117~120 (Decomposition) (Ethyl acetate-n-hexane) |
| 41 | n-Bu | 3,4-di(OMe)-phenyl | H | —COOH | 149~150 (Decomposition) (Ethyl acetate-n-hexane) |
| 42 | n-Bu | Ph | H | —COOH | Oily product (NMR 19) |
| 43 | n-Bu | 4-OMe-phenyl | H | —COOH | 157~158 (Decomposition) (Ethyl acetate-n-hexane) |
| 44 | n-Bu | 4-SMe-phenyl | H | —COOH | 133~135 (Decomposition) (Ethyl acetate-n-hexane) |
| 45 | n-Bu | 4-NMe₂-phenyl | H | —COOH | 165~166 (Decomposition) (Ethyl acetate-n-hexane) |
| 46 | n-Bu | 4-CF₃-phenyl | H | —COOH | 140~142 (Decomposition) (Ethyl acetate-n-hexane) |

TABLE 1-continued

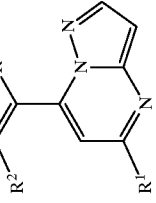

Me = methyl, Et = ethyl, i-Pr = isopropyl, n-Bu = n-butyl, Ph = phenyl

| Example No. | $R^1$ | $R^2$ | $R^3$ | $R^4$ | Melting point (° C.) (Recrystalization solvent) |
|---|---|---|---|---|---|
| 47 | n-Bu | 4-chlorophenyl | H | —COOH | 130–132 (Decomposition) (Ethyl acetate-n-hexane) |
| 48 | n-Bu | benzo[1,3]dioxol-5-yl | H | —COOH | 166–168 (Decomposition) (Ethyl acetate-n-hexane) |
| 49 | n-Bu | 2,6-dimethoxy-3-methylphenyl | H | —COOH | Oily product (NMR 20) |
| 50 | n-Bu | 6-methyl-2-naphthyl | H | —COOH | 110–113 (Decomposition) (Ethyl acetate-n-hexane) |
| 51 | n-Bu | 5-methyl-2-furyl | H | —COOH | 155–156 (Decomposition) (Ethyl acetate-n-hexane) |

TABLE 1-continued

Me = methyl, Et = ethyl, i-Pr = isopropyl, n-Bu = n-butyl, Ph = phenyl

| Example No. | R¹ | R² | R³ | R⁴ | Melting point (° C.) (Recrystalization solvent) |
|---|---|---|---|---|---|
| 52 | n-Bu | 2-pyridyl | H | —COOH | Hydrochloride, 130-132 (Decomposition) (Ethyl acetate) |
| 53 | Ph | 3,4,5-trimethoxyphenyl | H | —COOH | 206–208 (Decomposition) (Chloroform-ethyl acetate) |
| 54 | 2-thienyl | 3,4,5-trimethoxyphenyl | H | —COOH | 212–214 (Decomposition) (Chloroform-ethyl acetate) |
| 55 | n-Bu | 4-nitrophenyl | H | —COOH | 168–169 (Decomposition) (Ethyl acetate-n-hexane) |
| 56 | n-Bu | 4-fluorophenyl | H | —COOH | 158–159 (Decomposition) (Ethyl acetate-n-hexane) |
| 57 | n-Bu | 4-biphenylyl | H | —COOH | 160–161 (Decomposition) (Ethyl acetate-n-hexane) |

TABLE 1-continued

Me = methyl, Et = ethyl, i-Pr = isopropyl, n-Bu = n-butyl, Ph = phenyl

| Example No. | R¹ | R² | R³ | R⁴ | Melting point (° C.) (Recrystalization solvent) |
|---|---|---|---|---|---|
| 58 | n-Bu | 2,5-dimethoxy-methylphenyl (MeO, Me, OMe substituents) | H | —COOH | Oily product (NMR 21) |
| 59 | n-Bu | 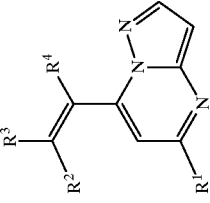 (styryl/β-methylstyrene) | H | —COOH | 195~196 (Decomposition) (Chloroform-ethyl acetate) |
| 60 | n-Bu | H | 4-(methylthio)phenyl (SMe) | H | 89–91 (n-Hexane) |
| 61 | n-Bu | H | 4-(trifluoromethyl)phenyl (CF₃) | H | 66–68 (n-Hexane) |
| 62 | n-Bu | H | 2-naphthyl | H | 134–136 (Decomposition) (Ethyl acetate-n-hexane) |

TABLE 1-continued

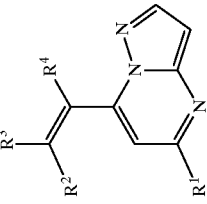

Me = methyl, Et = ethyl, i-Pr = isopropyl, n-Bu = n-butyl, Ph = phenyl

| Example No. | R¹ | R² | R³ | R⁴ | Melting point (° C.) (Recrystalization solvent) |
|---|---|---|---|---|---|
| 63 | Ph | H | 3,4,5-tri-OMe-4-methylphenyl | H | 119~121 (Ethyl acetate-n-hexane) |
| 64 | 2-thienyl | H | 3,4,5-tri-OMe-4-methylphenyl | H | 133~135 (Ethyl acetate-n-hexane) |
| 65 | n-Bu | H | 4-NO₂-phenyl | H | 125~127 (Ethyl acetate-n-hexane) |
| 66 | n-Bu | H | 3,4-di-OMe-4-methylphenyl | H | 89~91 (Ethyl acetate-n-hexane) |
| 67 | n-Bu | H | 4-F-phenyl | H | 71~73 (Ethanol-water) |
| 68 | n-Bu | H | 4-phenyl-phenyl | H | 117~119 (Toluene) |

TABLE 1-continued

Me = methyl, Et = ethyl, i-Pr = isopropyl, n-Bu = n-butyl, Ph = phenyl

| Example No. | R¹ | R² | R³ | R⁴ | Melting point (° C.) (Recrystallization solvent) |
|---|---|---|---|---|---|
| 69 | n-Bu | H | 2,5-(MeO)₂-3-Me-phenyl | H | 64–66 (Ethanol-n-hexane) |
| 70 (=31) | n-Bu | 3,5-(OMe)₂-4-Me-phenyl | H | —COOEt | 50–52 (n-Hexane) |
| 71 | n-Bu | 3,5-(OMe)₂-4-Me-phenyl | H | —COOCH₂SPh | Oily product (NMR 22) |
| 72 | n-Bu | 3,5-(OMe)₂-4-Me-phenyl | H | —COOCH₂-(3-OMe-phenyl) | Oily product (NMR 23) |
| 73 | n-Bu | 3,5-(OMe)₂-4-Me-phenyl | H | —COOCH₂-(4-Cl-phenyl) | 99–101 (Ethyl acetate-n-hexane) |

TABLE 1-continued
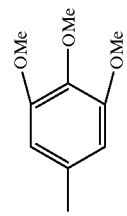
Me = methyl, Et = ethyl, i-Pr = isopropyl, n-Bu = n-butyl, Ph = phenyl
| Example No. | $R^1$ | $R^2$ | $R^3$ | $R^4$ | Melting point (° C.) (Recrystalization solvent) |
|---|---|---|---|---|---|
| 74 | n-Bu | 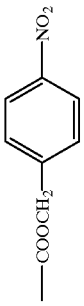 | H |  | 89–91 (Ethyl acetate-n-hexane) |
| 75 | n-Bu | 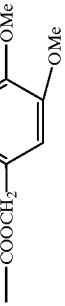 | H |  | Oily product (NMR 24) |
| 76 | n-Bu | 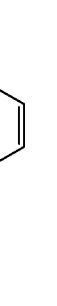 | H |  | 78–80 (Diethyl ether-n-hexane) |
| 77 | n-Bu |  | H | —COOPh | Oily product (NMR 25) |
| 78 | n-Bu |  | H | 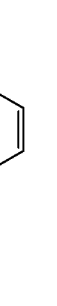 | 110–111 (Diethyl ether-n-hexane) |

TABLE 1-continued

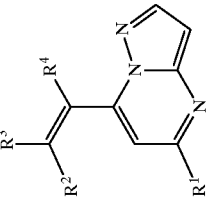

Me = methyl, Et = ethyl, i-Pr = isopropyl, n-Bu = n-butyl, Ph = phenyl

| Example No. | R¹ | R² | R³ | R⁴ | Melting point (° C.) (Recrystalization solvent) |
|---|---|---|---|---|---|
| 79 | n-Bu | 3,4,5-(OMe)₃-C₆H₂ | H | (acetoxymethylene-pyrazolopyrimidine structure) | 123–125 (Diethyl ether-n-hexane) |
| 80 | n-Bu | 3,4,5-(OMe)₃-C₆H₂ | H | —CONHEt | 150–152 (Ethyl acetate-n-hexane) |
| 81 | n-Bu | 3,4,5-(OMe)₃-C₆H₂ | H | —CONH₂ | 134–136 (Ethyl acetate-n-hexane) |
| 82 | n-Bu | 3,4,5-(OMe)₃-C₆H₂ | H | —CONHMe | 128–130 (Ethyl acetate-n-hexane) |

TABLE 1-continued

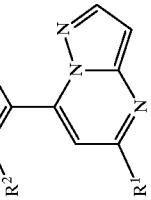

Me = methyl, Et = ethyl, i-Pr = isopropyl, n-Bu = n-butyl, Ph = phenyl

| Example No. | $R^1$ | $R^2$ | $R^3$ | $R^4$ | Melting point (° C.) (Recrystalization solvent) |
|---|---|---|---|---|---|
| 83 | n-Bu | 3,4,5-tri-OMe-phenyl | H | —CONH—i—Pr | 126~128 (Ethyl acetate-n-hexane) |
| 84 | n-Bu | 3,4,5-tri-OMe-phenyl | H | —CONHCH₂Ph | 154~155 (Diethyl ether) |
| 85 | n-Bu | 3,4,5-tri-OMe-phenyl | H | —CONHCH₂CO₂Et | 135~136 (Ethyl acetate-n-hexane) |
| 86 | n-Bu | 3,4,5-tri-OMe-phenyl | H | —CONH—CH(CH₂Ph)(CO₂Et) | 101~103 (Ethyl acetate-n-hexane) |
| 87 | n-Bu | 3,4,5-tri-OMe-phenyl | H | —CONH-(4-Cl-phenyl) | 161~163 (Ethyl acetate-n-hexane) |

TABLE 1-continued

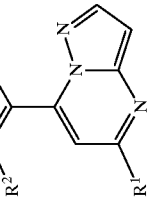

Me = methyl, Et = ethyl, i-Pr = isopropyl, n-Bu = n-butyl, Ph = phenyl

| Example No. | R¹ | R² | R³ | R⁴ | Melting point (° C.) (Recrystalization solvent) |
|---|---|---|---|---|---|
| 88 | n-Bu | H | 3,4,5-tri(OMe)-phenyl | —SOMe | 100~102 (Ethyl acetate-n-hexane) |
| 89 | n-Bu | 3,4,5-tri(OMe)-phenyl | H | —SO₂Me | 97~100 (Ethyl acetate-n-hexane) |
| 90 | n-Bu | H | 2,3-di(OMe)-phenyl | 2,4-di(OMe)-6-methyl-phenyl acetate | 127~118 (Ethyl acetate-n-hexane) |
| 91 | n-Bu | H | H | 2-methylphenyl acetate | 116~118 (Ethyl acetate-n-hexane) |

NMR1(CDCl$_3$, δ ppm):
0.89(3H, t, J=7.2), 1.2–1.4(2H, m), 1.5–1.6(2H, m), 2.65(2H, t, J=7.4), 6.49(1H, s), 6.64(1H, d, J=2.5), 7.08(1H, dd, J=12.6, 0.5), 7.14(1H, d, J=12.6), 8.10(1H, d, J=2.5).

NMR2(CDCl$_3$, δ ppm):
0.88(3H, t, J=7.2), 1.18(3H, t, J=7.2), 1.2–1.4(2H, m), 1.6–1.7(2H, m), 2.76(2H, t, J=7.4), 4.24(2H, q, J=7.2), 6.51(1H, s), 6.65(1H, d, J=2.5), 7.1–7.3(3H, m), 8.07(1H, d, J=2.5), 8.17(1H, s).

NMR3(CDCl$_3$, δ ppm):
0.91(3H, t, J=7.2), 1.17(3H, t, J=6.9), 1.2–1.4(2H, m) 1.6–1.8(2H, m), 2.80(2H, t, J=7.4), 3.75(3H, s), 4.22(2H, q, J=6.9), 6.58(1H, s), 6.65(1H, d, J=2.2), 6.68(2H, d, J=8.7), 6.96(2H, d, J=8.7), 8.06(1H, d, J=2.2), 8.11(1H, s).

NMR4(CDCl$_3$, δ ppm):
0.91(3H, t, J=7.4), 1.18(3H, t, J=6.9), 1.3–1.4(2H,m), 1.6–1.8(2H, m), 2.41(3H, s), 2.79(2H, t, J=7.7), 4.23(2H, q, J=6.9), 6.55(1H, s), 6.65(1H, d, J=2.2), 6.91(2H, d, J=8.7), 6.99(2H, d, J=8.7), 8.06(1H, d, J=2.2), 8.10(1H, s).

NMR5(CDCl$_3$, δ ppm):
0.92(3H, t, J=7.4), 1.17(3H, t, J=7.2), 1.3–1.4(2H, m), 1.7–1.8(2H, m), 2.81(2H, t, J=7.7), 2.94(6H, s), 4.21(2H, q, J=7.2), 6.42(2H, d, J=9.2), 6.64(1H, d, J=2.5), 6.65(1H, s), 6.88(2H, d, J=9.2), 8.04(1H, d, J=2.5), 8.07(1H, s).

NMR6(CDCl$_3$, δ ppm):
0.87(3H, t, J=7.4), 1.19(3H, t, J=6.9), 1.2–1.4(2H, m), 1.6–1.7(2H, m), 2.76(2H, t, J=7.4), 4.26(2H, q, J=6.9), 6.45(1H, s), 6.67(1H, d, J=2.5), 7.12(2H, d, J=7.9), 7.44(2H, d, J=7.9), 8.08(1H, d, J=2.5), 8.18(1H, s).

NMR7(CDCl$_3$, δ ppm):
0.91(3H, t, J=7.2), 1.17(3H, t, J=6.9), 1.3–1.4(2H, m), 1.7–1.8(2H, m), 2.81(2H, t, J=7.7), 4.22(2H, q, J=6.9), 5.91(2H, s), 6.36(1H, d, J=1.5), 6.58(1H, s), 6.6–6.7(3H, m), 8.06(1H, s), 8.06(1H, d, J=1.5).

NMR8(CDCl$_3$, δ ppm):
0.88(3H, t, J=7.4), 1.18(3H, t, J=7.2), 1.2–1.4(2H, m), 1.6–1.7(2H, m), 2.75(2H, t, J=7.7), 3.77(3H, s), 3.81(3H, s), 3.89(3H, s), 4.24(2H, q, J=7.2), 6.30(2H, d, J=1.0), 6.47(1H, s), 6.63(1H, d, J=2.2), 8.07(1H, d, J=2.2), 8.32(1H,s).

NMR9(CDCl$_3$, δ ppm):
0.80(3H, t, J=7.4), 1.21(3H, t, J=7.2), 1.2–1.3(2H, m), 1.6–1.7(2H, m), 2.74(2H, t, J=7.7), 4.27(2H, q, J=7.2), 6.54(1H, s), 6.68(1H, d, J=2.2), 6.90(1H, dd, J=1.7, 8.7), 7.4–7.6(3H, m), 7.6–7.8(3H, m), 8.09(1H, d, J=2.2), 8.33(1H, s).

NMR10(CDCl$_3$, δ ppm):
0.96(3H, t, J=7.4), 1.19(3H, t, J=7.2), 1.4–1.5(2H, m), 1.7–1.9(2H, m), 2.87(2H, t, J=7.7), 4.23(2H, q, J=7.2), 6.36(1H, dd, J=2.0, 3.5), 6.49(1H, d, J=3.5), 6.62(1H, d, J=2.2), 6.71(1H, s), 7.20(1H, d, J=2.0), 7.91(1H, s), 8.00(1H, d, J=2.2).

NMR11(CDCl$_3$, δ ppm):
1.23(3H, t, J=7.2), 3.44(6H, s), 3.77(3H, s), 4.28(2H, q, J=7.2), 6.26(2H, s), 6.79(1H, d, J=2.2), 7.21(1H, s),7.4–7.6(3H, m), 8.0–8.1(2H, m), 8.15(2H, brs).

NMR12(CDCl$_3$, δ ppm):
0.86(3H, t, J=7.4), 1.20(3H, t, J=7.2), 1.2–1.3(2H, m), 1.6–1.7(2H, m), 2.72(2H, t, J=7.4), 3.22(3H, s), 3.61(3H, s), 4.25(2H, q, J=7.2), 6.15(1H, d, J=2.7), 6.43(1H, s), 6.62(1H, d, J=2.2), 6.7–6.9(2H, m), 8.09(1H, d, J=2.2), 8.35(1H,s).

NMR13(CDCl$_3$, δ ppm):
0.91(3H, t, J=7.2), 1.21(3H, t, J=7.2), 1.3–1.4(2H, m), 1.6–1.8(2H, m), 2.80(2H, t, J=7.4), 3.30(3H, s), 3.83(3H, s), 4.25(2H, q, J=7.2), 6.22(1H, d, J=2.0), 6.60(1H, s), 6.65(1H, d, J=2.2), 6.70(1H, d, J=8.2), 6.79(1H, dd, J=2.0, 8.2), 8.06(1H, d, J=2.2), 8.12(1H,s).

NMR14(CDCl$_3$, δ ppm):
0.98(3H, t, J=7.2), 1.14(3H, t, J=7.2), 1.4–1.5(2H, m), 1.7–1.8(2H, m), 2.87(2H, t, J=7.7), 4.25(2H, q, J=7.2), 6.62(1H, d, J=2.2), 6.78(1H, s), 7.37(2H, d, J=8.7), 7.45(2H, d, J=8.7), 7.69(1H, s), 8.04(1H, d, J=2.2).

NMR15(CDCl$_3$, δ ppm):
0.90(3H, t, J=7.2), 1.18(3H, t, J=7.2), 1.2–1.4(2H, m), 1.6–1.7(2H, m), 2.78(2H, t, J=7.7), 4.24(2H, q, J=7.2), 6.50(1H, s), 6.66(1H, d, J=2.4), 6.94(2H, d, J=6.7), 7.14(2H, d, J=6.7), 8.07(1H, d, J=2.4), 8.11(1H, s).

NMR16(CDCl$_3$, δ ppm):
0.95(3H, t, J=7.4), 1.15(3H, t, J=6.9), 1.4–1.5(2H, m), 1.8–1.9(2H, m), 2.87(2H, t, J=7.7), 3.88(6H, s), 3.91(3H, s), 4.25(2H, q, J=6.9), 6.62(1H, d, J=2.5), 6.78(1H, s), 6.82(2H, s), 7.72(1H, s), 8.05(1H,d,J=2.5).

NMR17(CDCl$_3$, δ ppm):
0.90(3H, t, J=7.4), 1.22(3H, t, J=7.2), 1.3–1.4(2H, m), 1.6–1.8(2H, m), 2.79(2H, t, J=7.7), 4.27(2H, q, J=7.2), 6.55(1H, s), 6.61(1H, d, J=2.5), 7.10(1H, dd, J=4.2, 7.9), 7.11(1H, d, J=7.9), 7.53(1H, dt, J=1.7, 7.9), 7.99(1H, d, J=2.5), 8.16(1H, s), 8.27(1H, dd, J=1.7, 4.2).

NMR18(CDCl$_3$, δ ppm):
1.22(3H, t, J=7.2), 3.45(6H, s), 3.77(3H, s), 4.27(2H, q, J=7.2), 6.28(2H, s), 6.72(1H, d, J=2.5), 7.08(1H, s), 7.12(1H, dd, J=3.7, 4.9), 7.51(1H, dd, J=1.0, 4.9), 7.60(1H, dd, J=1.0, 3.7), 8.11(1H, d, J=2.5), 8.14(1H, s).

NMR19(CDCl$_3$, δ ppm):
0.87(3H, t, J=7.4), 1.2–1.4(2H, m), 1.6–1.7(2H, m), 2.76(2H, t, J=7.4), 6.54(1H, s), 6.68(1H, d, J=2.5), 6.9–7.0(2H, m), 7.1–7.3(3H, m), 8.10(1H, d, J=2.5), 8.22(1H, s).

NMR20(CDCl$_3$, δ ppm):
0.87(3H, t, J=7.4), 1.2–1.4(2H, m), 1.6–1.8(2H, m), 2.76(2H, t, J=7.4), 3.77(3H, s), 3.81(3H, s), 3.88(3H, s), 6.30(2H, s), 6.52(1H, s), 6.66(1H, d, J=2.0), 8.08(1H, d, J=2.0), 8.42(1H, s).

NMR21(CDCl$_3$, δ ppm):
0.85(3H, t, J=7.2), 1.2–1.3(2H, m), 1.5–1.7(2H, m), 2.72(2H, t, J=7.7), 3.20(3H, s), 3.61(3H, s), 6.13(1H, d, J=3.0), 6.48(1H, s), 6.65(1H, d, J=2.5), 6.73(1H, d, J=9.2), 6.80(1H, dd, J=3.0, 9.2), 8.12(1H, d, J=2.5), 8.45(1H, s).

NMR22(CDCl$_3$, δ ppm):
0.90(3H, t, J=7.2), 1.2–1.4(2H, m), 1.6–1.7(2H, m), 2.77(2H, t, J=7.7), 3.44(6H, s), 3.79(3H, s), 5.48(2H, s), 6.19(2H, s), 6.57(1H, s), 6.65(1H, d, J=2.5),7.1–7.2(5H, m), 8.06(1H, d, J=2.5), 8.14(1H, s).

NMR23(CDCl$_3$, δ ppm):
0.90(3H, t, J=7.4), 1.3–1.4(2H, m), 1.6–1.8(2H, m), 2.78(2H, t, J=7.7), 3.44(6H, s), 3.75(3H, s), 3.78(3H, s), 5.21(2H, s), 6.18(2H, s), 6.58(1H, s), 6.64(1H, d, J=2.2), 6.7–6.9(3H, m), 7.22(1H, t, J=7.9), 8.09(1H, d, J=2.2), 8.14(1H, s).

NMR24(CDCl$_3$, δ ppm):
0.89(3H, t, J=7.2), 1.2–1.4(2H, m), 1.6–1.7(2H, m), 2.78(2H, t, J=7.7), 3.44(6H, s), 3.77(6H, s), 3.78(3H, s), 3.82(3H, s), 5.16(2H, s), 6.18(2H, s), 6.38(2H, s), 6.59(1H, s), 6.64(1H, d, J=2.5), 8.08(1H, d, J=2.5), 8.14(1H, s).

NMR25(CDCl$_3$, δ ppm):
0.91(3H, t, J=7.4), 1.3–1.5(2H, m), 1.7–1.8(2H, m), 2.82(2H, t, J=7.7), 3.47(6H, s), 3,81(3H, s), 6.26(2H, s), 6.66(1H, d, J=2.2), 6.70(1H, s), 7.1–7.4(5H, m), 8.14(1H, d, J=2.2), 8.28(1H, s).

Example 92

The compound shown in Table 2 was prepared in a similar manner as in Example 60, using a compound prepared in a similar manner as in Reference Example 1 as a starting compound.

Examples 93–94

The compounds shown in Table 2 were prepared in a similar manner as in Examples 8 and 9.

Examples 95–98

The following compounds were prepared in a similar manner as in Reference Example 3.
Diethyl 1-(5-n-butylpyrazolo[1,5-a]pyrimidin-7-yl) benzylphosphonate;
Diethyl 1-(5-n-butylpyrazolo[1,5-a]pyrimidin-7-yl)-(4-chlorobenzyl)phosphonate.
The compounds shown in Table 2 were prepared in a similar manner as in Example 12, using the above compounds and (5-n-butylpyrazolo[1,5-a]pyrimidin-7-yl) trimethyl phosphonoacetate prepared in a similar manner as in Reference Example 1.

Examples 99–100

The compounds shown in Table 2 were prepared by hydrolyzing the compounds obtained in Examples 85 and 86 in a similar manner as in Example 40.

Examples 101–105

The following compounds were prepared in a similar manner as in Example 12, using (5-methylpyrazolo[1,5-a]pyrimidin-7-yl)trimethyl phosphonoacetate, (5-ethylpyrazolo[1,5-a]pyrimidin-7-yl)trimethyl phosphonoacetate and (5-n-propylpyrazolo[1,5-a]pyrimidin-7-yl) trimethyl phosphonoacetate prepared in a similar manner as in Reference Example 1.
(E) methyl 2-(5-methylpyrazolo[1,5-a]pyrimidin-7-yl)-3-(3,4,5-trimethoxyphenyl)acrylate
(E) methyl 2-(5-ethylpyrazolo[1,5-a]pyrimidin-7-yl)-3-(3,4,5-trimethoxyphenyl)acrylate
(E) methyl 2-(5-n-propylpyrazolo[1,5-a]pyrimidin-7-yl)-3-(3,4,5-trimethoxyphenyl)acrylate.
The above compounds and the compounds obtained in Examples 97 and 98 were hydrolyzed in a similar manner as in Example 40, thus giving the compounds shown in Table 2.

Example 106–108

The compounds obtained in Examples 101–103 were decarboxylated in a similar manner as in Example 60, thus giving the compounds shown in Table 2.

Example 109

Preparation of (E) 2-(5-n-butylpyrazolo[1,5-a]pyrimidin-7-yl)-3-(4-hydroxy-3,5-dimethoxyphenyl)acrylic acid
2 g of the compound obtained in Example 105 was dissolved in 20 ml of ethanol. To the solution was added 0.2 g of 5% palladium-carbon, followed by purging the reaction system with hydrogen and stirring at room temperature for 30 minutes (hydrogen consumption: about 94 ml). After completion of the reaction, 5% palladium-carbon was separated by filtration and the filtrate was concentrated. The residue was purified by silica gel column chromatography (eluent; chloroform yl)trimethyl phosphonoacetate obtained in a similar manner as in Reference Example 1 was reacted with 3-benzyloxy-4,5-dimethoxybenzaldehyde in a similar manner as in Example 12. (E) methyl 2-(5-n-butylpyrazolo [1,5-a]pyrimidin-7-yl)-3-(3-benzyloxy-4,5-dimethoxyphenyl)acrylic acid was obtained.
Subsequently, the compound was hydrolyzed in a similar manner as in Example 109, thus giving the compound shown in Table 2.

TABLE 2

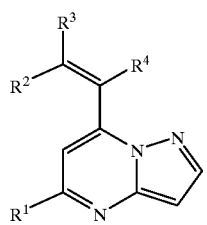

Me = methyl, Et = ethyl, i-Pr = isopropyl, n-Pr = n-propyl, n-Bu = n-butyl, Ph = phenyl

| Example No. | R¹ | R² | R³ | R⁴ | Melting point (° C.) (Recrystalization solvent) |
|---|---|---|---|---|---|
| 92 | n-Bu | H | 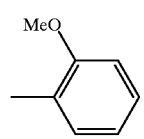 | H | 64~66 (n-Hexane) |
| 93 | n-Bu | H | —C≡C—Ph | H | 79~83 (Ethanol-water) |
| 94 | n-Bu | —C≡C—Ph | H | H | 49~50 (Ethanol-water) |

TABLE 2-continued

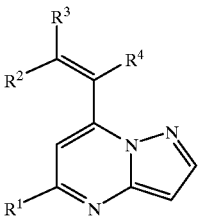

Me = methyl, Et = ethyl, i-Pr = isopropyl, n-Pr = n-propyl, n-Bu = n-butyl, Ph = phenyl

| Example No. | R¹ | R² | R³ | R⁴ | Melting point (° C.) (Recrystalization solvent) |
|---|---|---|---|---|---|
| 95 | n-Bu | 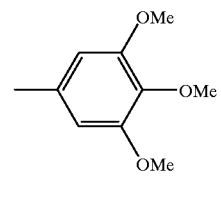 | H | Ph | 103–105 (Diisopropyl ether) |
| 96 | n-Bu | 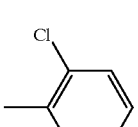 | H | 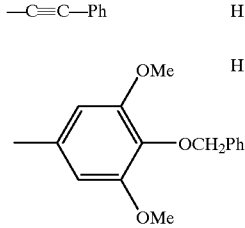 | 89~92 (Diethyl ether-n-hexane) |
| 97 | n-Bu | —C≡C—Ph | H | —COOMe | 100~103 (Diisopropyl ether) |
| 98 | n-Bu | 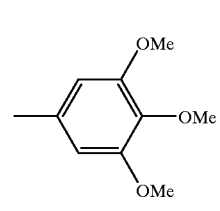 | H | —COOMe | 134~137 (Methanol) |
| 99 | n-Bu | 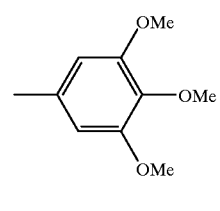 | H | —CONHCH₂CO₂H | >113 (Decomposition) (Ethyl acetate-n-hexane) |
| 100 | n-Bu | 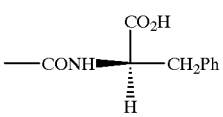 | H | 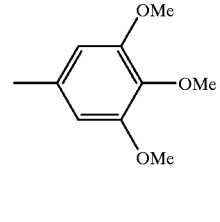 | 127~130 (Diethyl ether-n-hexane) |
| 101 | Me |  | H | —COOH | >172 (Decomposition) (Ethyl acetate-n-hexane) |

TABLE 2-continued

[Structure: pyrazolo[1,5-a]pyrimidine with R¹ at 5-position and vinyl group =C(R²)-C(R³)=CR⁴ at 7-position, where vinyl carbons bear R², R³, R⁴]

Me = methyl, Et = ethyl, i-Pr = isopropyl, n-Pr = n-propyl, n-Bu = n-butyl, Ph = phenyl

| Example No. | R¹ | R² | R³ | R⁴ | Melting point (° C.) (Recrystalization solvent) |
|---|---|---|---|---|---|
| 102 | Et | 3,4,5-tri(OMe)phenyl | H | —COOH | >165 (Decomposition) (Ethyl acetate-n-hexane) |
| 103 | n-Pr | 3,4,5-tri(OMe)phenyl | H | —COOH | >175 (Decomposition) (Ethyl acetate-n-hexane) |
| 104 | n-Bu | —C≡C—Ph | H | —COOH | >155 (Decomposition) (Ethyl acetate-n-hexane) |
| 105 | n-Bu | 3,5-di(OMe)-4-(OCH₂Ph)phenyl | H | —COOH | >155 (Decomposition) (Ethyl acetate-n-hexane) |
| 106 | Me | H | 3,4,5-tri(OMe)phenyl | H | 157~160 (Ethanol) |
| 107 | Et | H | 3,4,5-tri(OMe)phenyl | H | 164~166 (Ethyl acetate-n-hexane) |
| 108 | n-Pr | H | 3,4,5-tri(OMe)phenyl | H | 96~99 (Ethyl acetate-n-hexane) |

TABLE 2-continued

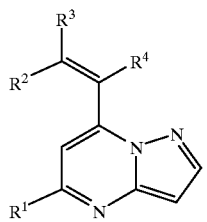

Me = methyl, Et = ethyl, i-Pr = isopropyl, n-Pr = n-propyl, n-Bu = n-butyl, Ph = phenyl

| Example No. | $R^1$ | $R^2$ | $R^3$ | $R^4$ | Melting point (° C.) (Recrystalization solvent) |
|---|---|---|---|---|---|
| 109 | n-Bu | ![2,6-dimethoxy-3-hydroxyphenyl] | H | —COOH | >152 (Decomposition) (Ethyl acetate-n-hexane) |
| 110 | n-Bu | ![2-hydroxy-3,4-dimethoxyphenyl] | H | —COOH | >185 (Decomposition) (Ethyl acetate-n-hexane) |

Given below are Formulation Examples for manufacturing pharmaceutical compositions containing the compound of the invention as an active ingredient.

Formulation Example 1
Manufacture of Tablets

Tablets (1000 tables), each containing as an active ingredient 250 mg of the compound of the invention obtained in Example 10, were manufactured according to the following formulation:

| Component | Amount (g) |
|---|---|
| Compound of the invention obtained in Example 10 | 250 |
| Lactose (Japanese pharmacopoeia) | 33.5 |
| Corn starch (Japanese pharmacopoeia) | 16.5 |
| Carboxymethyl cellulose calcium (Japanese pharmacopoeia) | 12.5 |
| Methyl cellulose (Japanese pharmacopoeia) | 6.0 |
| Magnesium stearate (Japanese pharmacopoeia) | 1.5 |
| Total | 320.0 |

According to the above formulation, the compound of the invention obtained in Example 10, lactose, corn starch and carboxymethyl cellulose calcium were well blended and granulated using aqueous methyl cellulose solution. The granulated mixture was passed through a 24-mesh sieve, and the granules under the sieve were mixed with magnesium stearate and compression-molded to give the desired tablets.

Formulation Example 2
Manufacture of capsules

Hard gelatin capsules (1000 capsules), each containing as an active ingredient 250 mg of the compound of the invention obtained in Example 40, were manufactured according to the following formulation:

| Component | Amount (g) |
|---|---|
| Compound of the invention obtained in Example 40 | 250 |
| Crystalline cellulose (Japanese pharmacopoeia) | 30 |
| Corn starch (Japanese pharmacopoeia) | 17 |
| Talc (Japanese pharmacopoeia) | 2 |
| Magnesium stearate (Japanese pharmacopoeia) | 1 |
| Total | 300 |

According to the above formulation, the ingredients were finely pulverized and blended to give a homogeneous mixture. This mixture was filled into proper-sized gelatin capsule shells for oral administration to provide the desired capsules.

Given below are Pharmacological Test Examples in which the compounds of the invention were tested.

Pharmacological Test Example 1

Using 6-week-old male S.D. rats (7 rats in each group), the pain threshold of each rat's left hind paw plantar was measured using an Analgesy-Meter (product of Unicom) in accordance with the Randall-Sellitto method [Randall, L. O. and Sellitto, J. J., Arch. Int. Pharmacodyn., 111, 409 (1957)]. The value thus obtained was termed "pre-value".

One hour after the measurement of the pre-value, a 5% gum arabic suspension containing the compound of the invention was orally administered to the rats of the test group in an amount of 10 ml/kg, whereas a 5% gum arabic suspension (not containing the compound of the invention) was orally administered to the rats of the control group in an amount of 10 ml/kg.

One hour later, a physiological saline solution containing substance P (25 ng/0.1 ml) was subcutaneously injected into the left hind paw plantar of each rat.

The pain threshold of each rat's left hind paw was measured in the same manner as above at predetermined time intervals from the substance P injection. The measured value was termed "post-value".

The recovery (%) of the pain threshold was calculated from the post-values and the pre-values of the test group and the control group, by means of the following formula:

$$\text{Recovery of pain threshold (\%)} = \frac{(\text{Test group average post-value}) - (\text{Control group average post-value})}{(\text{Control group average pre-value}) - (\text{Control group average post-value})} \times 100$$

Table 3 shows the results (the highest recovery %).

TABLE 3

| Example No. | Recovery (%) | Time of measurement (minutes later) |
|---|---|---|
| 1 | 47.8 | 60 |
| 8 | 36.2 | 30 |
| 10 | 58.7 | 60 |
| 12 | 41.5 | 60 |
| 40 | 47.2 | 60 |
| 43 | 46.3 | 30 |
| 45 | 40.4 | 60 |
| 46 | 48.9 | 60 |
| 47 | 57.1 | 30 |
| 62 | 50.0 | 30 |
| 65 | 30.1 | 30 |
| 66 | 32.2 | 60 |
| 74 | 50.3 | 15 |
| 78 | 60.1 | 15 |
| 79 | 41.2 | 60 |
| 98 | 44.7 | 60 |
| 99 | 32.2 | 60 |
| 103 | 54.8 | 60 |
| 105 | 50.4 | 60 |
| 109 | 52.1 | 60 |
| 110 | 58.0 | 60 |

The results presented in Table 3 clearly demonstrate that the compounds of the present invention have potent analgesic effects.

Industrial Applicability

The pyrazolo[1,5-a]pyrimidine derivatives according to the present invention have potent analgesic effects and are useful as analgesics.

What is claimed is:

1. A pyrazolo[1,5-a]pyrimidine derivative represented by the following formula (1)

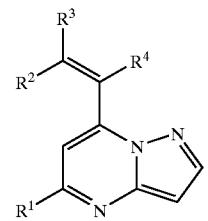

(1)

wherein $R^1$ is lower alkyl, phenyl or thienyl;

one of $R^2$ and $R^3$ is hydrogen and the other is naphthyl, furyl, pyridyl, styryl, phenylethynyl, substituted phenyl having 1 to 3 substituents selected from the group consisting of lower alkoxy, phenyl-lower alkoxy and hydroxyl, or phenyl which may have a substituent selected from the group consisting of lower alkylthio, N,N-di-lower alkylamino, halogen-substituted lower alkyl, phenyl, nitro, methylenedioxy and halogen;

$R^4$ is hydrogen, lower alkylthio, lower alkylsulfinyl, lower alkylsulfonyl, carboxyl, lower alkoxy-carbonyl, lower alkyl, phenylthiomethoxycarbonyl, substituted benzyloxycarbonyl having 1 to 3 substituents selected from the group consisting of lower alkoxy, halogen and nitro, phenoxycarbonyl which may have halogen or nitro as a substituent, carbamoyl, N-lower alkyl-carbamoyl, N-benzyl-carbamoyl, N-(lower alkoxy-carbonyl-lower alkyl)carbamoyl, N-(carboxy-lower alkyl)carbamoyl, N-halophenylcarbamoyl, N-(1-lower alkoxy-carbonyl-2-phenylethyl)carbamoyl, N-(1-carboxy-2-phenylethyl)carbamoyl, phenyl which may have halogen as a substituent, or the group

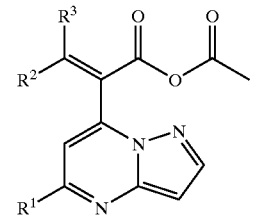

wherein $R^1$, $R^2$ and $R^3$ are as defined above;

when $R^2$ is hydrogen, $R^3$ and $R^4$ may conjointly represent a group represented by

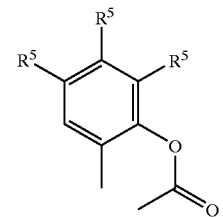

wherein the $R^5$s are the same or different and independently represent hydrogen or lower alkoxy.

2. The pyrazolo[1,5-a]pyrimidine derivative according to claim 1 which is selected from:

(i) compounds wherein $R^1$ is lower alkyl; and (ii) compounds wherein $R^1$ is phenyl or thienyl, one of $R^2$ and $R^3$ is hydrogen and the other is substituted phenyl having 1 to 3 lower alkoxy groups as substituents and $R^4$ is hydrogen, carboxyl or lower alkoxy-carbonyl.

3. The pyrazolo[1,5-a]pyrimidine derivative according to claim 2 which is selected from:

(1a) compounds defined in (i) of claim 2 wherein $R^1$ is lower alkyl and $R^4$ is hydrogen, carboxyl or lower alkoxy-carbonyl;

(1b) compounds defined in (i) of claim 2 wherein $R^1$ is lower alkyl and one of $R^2$ and $R^3$ is hydrogen and the other is phenyl having 1 to 3 lower alkoxy groups as substituents, $R^4$ is lower alkylthio, lower alkylsulfinyl, lower alkylsulfonyl, lower alkyl, phenylthiomethoxycarbonyl, substituted benzyloxycarbonyl having 1 to 3 substituents selected from the group consisting of lower alkoxy, halogen and nitro, phenoxycarbonyl which may have halogen or nitro as a substituent, carbamoyl, N-lower alkyl-carbamoyl, N-benzylcarbamoyl, N-(lower alkoxy-carbonyl-lower alkyl)carbamoyl, N-(carboxy-lower alkyl)carbamoyl, N-halophenylcarbamoyl, N-(1-lower alkoxy-carbonyl-2-phenylethyl)carbamoyl, or the group

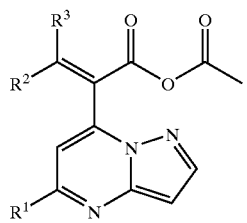

wherein $R^1$, $R^2$ and $R^3$ are as defined in formula (1); and (1c) compounds defined in (i) of claim 2 wherein $R^1$ is lower alkyl and $R^2$ is hydrogen and $R^3$ and $R^4$ conjointly represent a group represented by

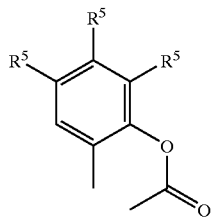

wherein the $R^5$s are the same or different and independently represent hydrogen or lower alkoxy.

4. The pyrazolo[1,5-a]pyrimidine derivative according to claim 3 wherein $R^1$ is n-butyl.

5. The pyrazolo[1,5-a]pyrimidine derivative according to claim 2 which is selected from the compounds (ii) of claim 2 wherein $R^1$ is phenyl or thienyl, one of $R^2$ and $R^3$ is hydrogen and the other is phenyl having 1 to 3 lower alkoxy groups as substituents and $R^4$ is hydrogen, carboxyl or lower alkoxy-carbonyl.

6. The pyrazolo[1,5-a]pyrimidine derivative according to claim 1 which is selected from:

(i) compounds wherein $R^1$ is n-butyl, $R^2$ is hydrogen, $R^3$ is naphthyl, pyridyl, phenyl having 1 to 3 lower alkoxy groups as substituents or halogen-substituted phenyl and $R^4$ is hydrogen or lower alkylthio; and (ii) compounds wherein $R^1$ is n-propyl or n-butyl, $R^2$ is substituted phenyl having 1 to 3 substituents selected from the group consisting of lower alkoxy, phenyl-lower alkoxy and hydroxyl, or phenyl which may have a substituent selected from the group consisting of N,N-di-lower alkylamino, halogen-substituted lower alkyl and halogen, $R^3$ is hydrogen and $R^4$ is carboxyl, lower alkoxy-carbonyl, phenylthiomethoxycarbonyl, substituted benzyloxycarbonyl having 1 to 3 substituents selected from the group consisting of lower alkoxy, halogen and nitro, phenoxycarbonyl which may have halogen or nitro as a substituent, or the group

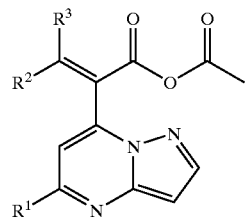

wherein $R^1$, $R^2$ and $R^3$ are as defined above.

7. The pyrazolo[1,5-a]pyrimidine derivative according to claim 6 which is selected from:

(i) compounds defined in (i) of claim 6 wherein $R^3$ is pyridyl and $R^4$ is hydrogen; and (ii) compounds defined in (ii) of claim 6 wherein $R^1$ is n-butyl, $R^2$ is phenyl having three lower alkoxy groups as substituents or phenyl having two lower alkoxy groups and one hydroxyl group as substituents.

8. The pyrazolo[1,5-a]pyrimidine derivative according to claim 7 which is selected from:

(i) compounds defined in (i) of claim 7 wherein $R^3$ is 2-pyridyl; and (ii) compounds defined in (ii) of claim 7 wherein $R^2$ is 3,4,5-trimethoxyphenyl and $R^4$ is carboxyl.

9. A pharmaceutical composition comprising an effective amount of the pyrazolo[1,5-a]pyrimidine derivative of claim 1 and a pharmaceutically acceptable carrier.

10. The pharmaceutical composition according to claim 9 which is an analgesic composition.

11. A method for relieving pain in a patient in need of such pain relief, which comprises administering to the patient an effective amount of the pyrazolo[1,5-a]pyrimidine derivative of claim 1.

* * * * *